(12) United States Patent
Uemura et al.

(10) Patent No.: US 8,481,484 B2
(45) Date of Patent: Jul. 9, 2013

(54) CYCLIC HEPTAPEPTIDE AND USE OF THE SAME

(75) Inventors: Daisuke Uemura, Nagoya (JP);
Kenichiro Shimokawa, Nagoya (JP);
Yoshiaki Iwase, Nagoya (JP); Kaoru Yamada, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 503 days.

(21) Appl. No.: 12/675,485

(22) PCT Filed: Jun. 6, 2008

(86) PCT No.: PCT/JP2008/060486
§ 371 (c)(1),
(2), (4) Date: Jul. 6, 2010

(87) PCT Pub. No.: WO2009/028248
PCT Pub. Date: Mar. 5, 2009

(65) Prior Publication Data
US 2010/0286363 A1 Nov. 11, 2010

(30) Foreign Application Priority Data
Aug. 27, 2007 (JP) .................. 2007-220131

(51) Int. Cl.
*A61K 38/00* (2006.01)
*A61K 38/12* (2006.01)
*A61P 3/04* (2006.01)
*C07K 7/64* (2006.01)

(52) U.S. Cl.
USPC .............. 514/4.8; 514/4.9; 530/317; 530/329

(58) Field of Classification Search
None
See application file for complete search history.

(56) References Cited

FOREIGN PATENT DOCUMENTS

| JP | 06-293796 A | 10/1994 |
| JP | 11-130656 A | 5/1999 |
| JP | 2002-037738 A | 2/2002 |
| JP | 2004-075640 A | 3/2004 |
| JP | 2005-220074 A | 8/2005 |
| JP | 2006-213648 A | 8/2006 |

OTHER PUBLICATIONS

Yasuji Furutani et al., "B$_3$ adrenaline juyotai," Protein Nucleic Acid Enzyme 2000, 45, pp. 935-940 and English concise explanation thereof.
David A. Langs, "Ab Initio Direct Methods: Practical Advice for Getting Beyond the First 300 Atoms," Acta Cryst., D49, 1993, pp. 158-167.
R. Miller et al., Molecular structures of two crystalline forms of the cyclic heptapeptide antibiotic ternatin, cyclo[-β-OH-D-Leu-D-Ile-(*N*Me)Ala-(*N*Me)Leu-Leu-(*N*Me)Ala-D-(*N*Me)Ala-], International Journal of Peptide & Protein Research, 1993, 42, pp. 539-549.
Kenichiro Shimokawa et al., "(−)-Ternatin, a highly N-methylated cyclic heptapeptide that inhibits fat accumulation: structure and synthesis," Tetrahedron Letters, 2006, 47, pp. 4445-4448.
Kenichiro Shimokawa et al., "Convergent synthesis and in vivo inhibitory effect on fat accumulation of (−)-ternatin, a highly N-methylated cyclic peptide," Bioorg. Med. Chem Lett 17, 2007, pp. 4447-4449.
Kenichiro Shimokawa et al., "Synthesis and inhibitory effect on fat accumulation of (−)-ternatin derivatives modified in the β-OH-D-Leu$^7$ moiety," Org. Biomol. Chem., vol. 6, 2008, pp. 58-60.
International Search Report dated Jul. 8, 2008, issued on PCT/JP2008/060486.

*Primary Examiner* — Noble Jarrell
(74) *Attorney, Agent, or Firm* — Edwards Wildman Palmer LLP; James E. Armstrong, IV; Edmund J. Koundakjian

(57) ABSTRACT

A novel cyclic heptapeptide that is useful as a preadipocyte differentiation-inhibitory agent or an adipocyte fat accumulation-inhibitory agent, and the use of such agents, are provided. A novel cyclic heptapeptide represented by the following formula is provided.

[Chemical formula 1]

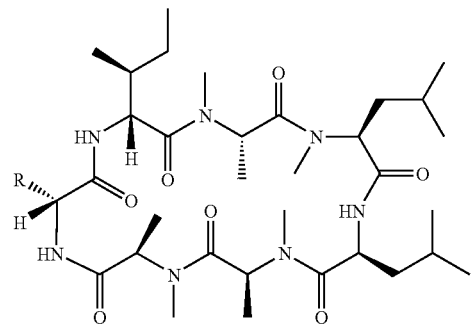

wherein R is $CH_3$, $CH_2CH(CH_3)_2$, $CH_2OCH_2C_6H_5$, $CH(OH)CH_3$, or $CH_2OH$.

20 Claims, 7 Drawing Sheets

FIG. 7

| | 1 | 2 | 3 | 4 | 5 | 6 | 7 | EC50 (μg/mL) | IC50 (μg/mL) | IC50/EC50 |
|---|---|---|---|---|---|---|---|---|---|---|
| | D-allo-Ile | NMe-L-Ala | NMe-L-Leu | L-Leu | NMe-L-Ala | NMe-D-Ala | β-OH-D-Leu | 0.02 | 0.21 | 10.5 |
| 1a | - | - | - | - | - | - | D-Ala | 9.3 | >100 | >10.7 |
| 1b | - | - | - | - | - | - | D-Leu | 0.16 | 2.4 | 15 |
| 1c | - | - | - | - | - | - | D-Ser(Obn) | 4.6 | 70 | 15.2 |
| 1d | - | - | - | - | - | - | D-Thr | 2.3 | 36 | 15.6 |
| 1e | - | - | - | - | - | - | D-Ser | 8.2 | 100 | 12.2 |

CYCLIC HEPTAPEPTIDE AND USE OF THE SAME

The present invention relates to a novel cyclic heptapeptide and use of the same. The cyclic heptapeptide of the present invention has an inhibitory effect on the differentiation of preadipocytes and an inhibitory effect on fat accumulation against adipocytes.

BACKGROUND ART

Obesity, which is caused by the abnormal accumulation of fat in fat tissue and in various organs in the human body, is considered to be closely associated with the onset of various lifestyle-related diseases such as hypertension, arteriosclerosis, and diabetes. Further, obesity is becoming a problem in the field of cosmetics because it alters body proportions and significantly impairs the outward appearance.

Obesity is said to be caused by the accumulation of fat due to the consumption of excess calories over calories used, which is the result of predisposing factors such as constitutional, dietary, mental, central, and metabolic factors, a lack of exercise, and the like. In obesity, the amount of fat that accumulates in individual adipocytes, namely triglyceride, is increased and the adipocytes are enlarged. Furthermore, it has recently been elucidated that the number of adipocytes continues to increase after adulthood. Thus, it is anticipated that obesity can be improved by decreasing the number of mature adipocytes by inhibiting the differentiation of preadipocytes into mature adipocytes, and that the progression of obesity can be suppressed by inhibiting fat accumulation in mature adipocytes.

Examples of medicines, food, or cosmetic agents that exert an anti-obesity effect by inhibiting the increase in the number of adipocytes include one that contains preadipocyte differentiation-inhibitory peptides as an active ingredient (refer to Patent Document 1) and one that contains activated whey as an active ingredient (refer to Patent Document 2). Further, an attempt has been made to apply ω-3-based polyunsaturated fatty acids as an active agent to the skin (refer to Patent Document 3). Also, it was reported that arterenol acted on β3 adrenaline distributed in adipocytes to trigger the activation of protein kinase A (PKA) and hormone-sensitive lipase (HSL), which promoted the degradation of triglyceride that had accumulated as an oil droplet (refer to Non-Patent Document 1).

The present inventors have continuously studied medicines and other products that exhibit an anti-obesity effect by inhibiting the differentiation of preadipocytes or inhibiting fat accumulation in adipocytes, and have found a preadipocyte differentiation-inhibitory agent containing an active ingredient extracted from a specific mushroom or plant (Patent Document 4), an adipocyte differentiation-inhibitory agent containing ternatin: cyclo[-D-Ile1-(N-Me)-L-Ala2-(N-Me)-L-Leu3-L-Leu4-(N-Me)-L-Ala5-(N-Me)-D-Ala6-β-OH-D-Leu7-], which is a cyclic heptapeptide, as an active ingredient (Patent document 5), and an adipocyte differentiation-inhibitory agent containing bisabololoxide-A-β-glucoside, which is a plant ingredient, as an active ingredient (Patent Document 6). However, before cyclic peptides with the aforementioned properties can be put to practical application, various tests as well as the development and investigation of analogous compounds that may be even more efficacious are necessary. Thus, the development of an inexpensive, high-yield production method is needed because the amount of cyclic peptides as described above that can be obtained from natural sources has been insufficient. The physical properties and results of the X-ray crystal structure analysis of ternatin have been reported (refer to Patent Document 7, Non-Patent Documents 2 and 3).

In general, methods for the synthesis of a peptide (production method) include both solid-phase and solution-phase methods. Both methods have good and bad points. Although the present inventors initially synthesized ternatin by a solid-phase method and determined its stereochemical structure (Non-Patent Document 4), the yield was low, a reagent used was expensive, the method was inefficient because every time an analogous compound in which some of the constituent amino acids were replaced was synthesized, it needed to be synthesized sequentially from one end, and the like.

[Patent Document 1] Japanese Patent Application Laid-Open No. 6-293796

[Patent Document 2] Japanese Patent Application Laid-Open No. 2002-37738

[Patent Document 3] Japanese Patent Application Laid-Open No. 11-130656

[Patent Document 4] Japanese Patent Application Laid-Open No. 2004-075640

[Patent Document 5] Japanese Patent Application Laid-Open No. 2005-220074

[Patent Document 6] Japanese Patent Application Laid-Open No. 2006-213648

[Patent Document 7] Russian Patent No. N517198, Specification, 1974.

[Non-Patent Document 1] Protein Nucleic Acid Enzyme 2000, 45, 935-940.

[Non-Patent Document 2] Acta Crystallographica Section D, 1993, 49, 158-167.

[Non-Patent Document 3] International Journal of Peptide & Protein Research, 1993, 42, 539-549.

[Non-Patent Document 4] Tetrahedron Letters, 2006, 47, 4445.

DISCLOSURE OF THE INVENTION

Problem to be Solved by the Invention

Against this background, the aim of the present invention is to provide a novel cyclic heptapeptide that is useful as a preadipocyte differentiation-inhibitory agent or an adipocyte fat accumulation-inhibitory agent, and to describe use of the agent.

Means for Solving the Problems

The present inventors conducted thorough research to solve the aforementioned problems. As a result, they successfully developed a method for synthesizing the desired cyclic heptapeptides simply and inexpensively in high yield, and further, they found that a novel cyclic heptapeptide in which some of the constituent amino acids of ternatin were replaced exhibited a preadipocyte differentiation-inhibitory effect or an adipocyte fat accumulation-inhibitory effect, thereby completing the present invention as listed hereinbelow.

[1] A cyclic heptapeptide represented by the following formula;

[Chemical formula 1]

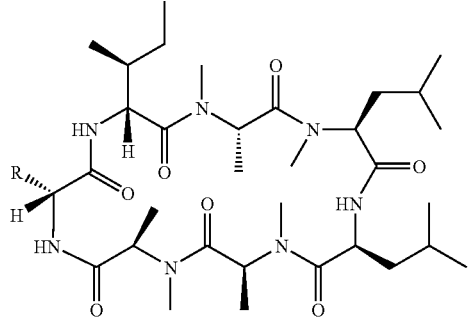

wherein R is $CH_3$, $CH_2CH(CH_3)_2$, $CH_2OCH_2C_6H_5$, $CH(OH)CH_3$, or $CH_2OH$.

[2] A preadipocyte differentiation-inhibitory agent composed of the cyclic heptapeptide according to [1].

[3] An adipocyte fat accumulation-inhibitory agent composed of the cyclic heptapeptide according to [1].

[4] A composition containing the cyclic heptapeptide according to [1] as an active ingredient.

[5] The composition according to [4], wherein the composition is a medicine, food, or cosmetic agent.

[6] Use of the cyclic heptapeptide according to [1] in the production of a preadipocyte differentiation-inhibitory agent, an adipocyte fat accumulation-inhibitory agent, a medicine, food, or cosmetic agent.

BRIEF DESCRIPTION OF THE DRAWINGS

FIG. 7 shows the results of an activation assay with the novel cyclic heptapeptide. In the table, "-" indicates that amino acids in the corresponding positions are the same as those in ternatin. EC50 refers to the 50% effective concentration (the compound concentration at which the fat accumulation rate is 50%), and IC50 refers to the 50% inhibitory concentration (the compound concentration at which the cell survival rate is 50%).

BEST MODE FOR CARRYING OUT THE INVENTION

Figure 1:
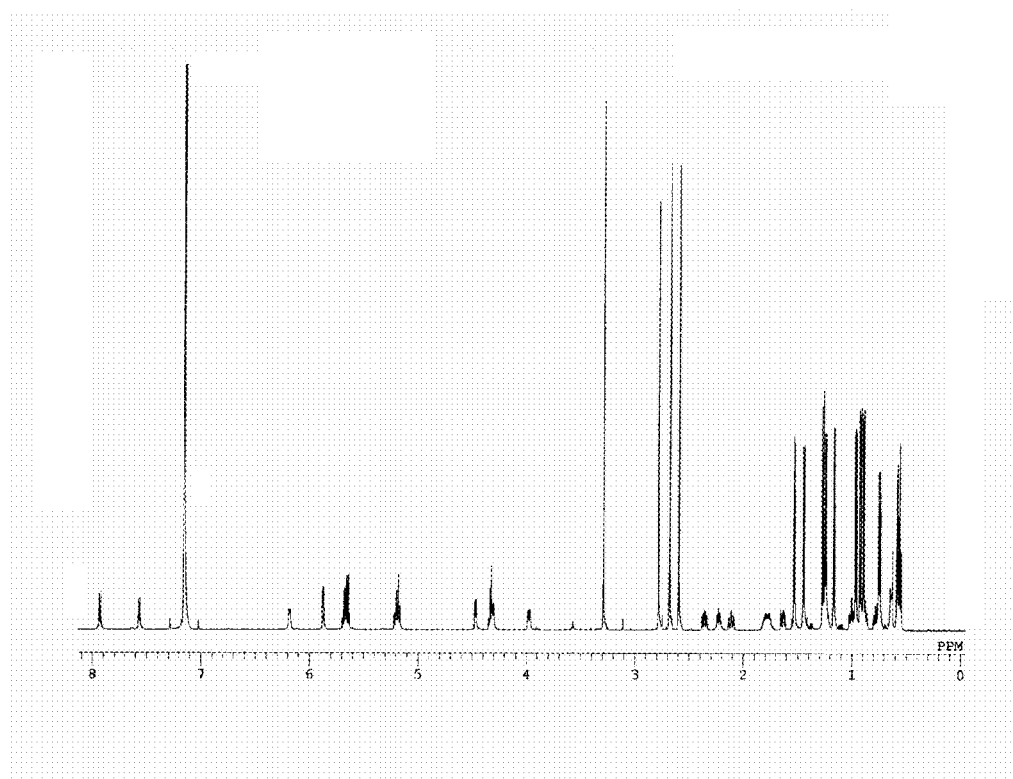
FIG. 1 is a $^1H$ NMR spectrum of ternatin(1) ($C_6D_6$, 600 MHz).

The cyclic heptapeptide of the present invention (SEQ ID NO: 1) is represented by the following formula (formula 1).

[Chemical formula 2]

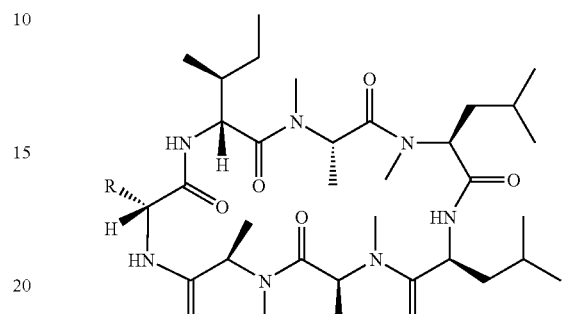

wherein R is $CH_3$, $CH_2CH(CH_3)_2$, $CH_2OCH_2C_6H_5$, $CH(OH)CH_3$, or $CH_2OH$. In the present specification, a compound in which R is $CH_3$ (SEQ ID NO: 2) is called cyclic heptapeptide (1a), a compound in which R is $CH_2CH(CH_3)_2$ (SEQ ID NO: 3) is called cyclic heptapeptides (1b), a compound in which R is $CH_2OCH_2C_6H_5$ (SEQ ID NO: 4) is called cyclic heptapeptides (1c), a compound in which R is $CH(OH)CH_3$ (SEQ ID NO: 5) is called cyclic heptapeptides (1d), and a compound in which R is $CH_2OH$ (SEQ ID NO: 6) is called cyclic heptapeptides (1e). The above five kinds of cyclic heptapeptides share the characteristic that an amino acid at the 7-position of ternatin is replaced by another amino acid. The amino acid at the 7-position of cyclic heptapeptide (1a) is D-Ala, the amino acid at the 7-position of cyclic heptapeptides (1b) is D-Leu, the amino acid at the 7-position of cyclic heptapeptides (1c) is D-Ser(OBn), the amino acid at the 7-position of cyclic heptapeptides (1d) is D-Thr, and the amino acid at the 7-position of cyclic heptapeptides (1e) is D-Ser. The structural formulas of cyclic heptapeptides (1a), cyclic heptapeptides (1b), cyclic heptapeptides (1c), cyclic heptapeptides (1d), and cyclic heptapeptides (1e) are listed hereinbelow in this order.

[Chemical formula 3]

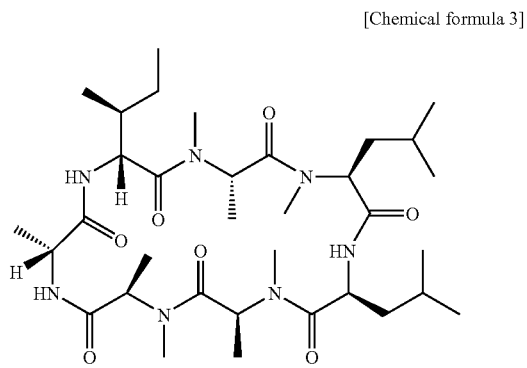

-continued

[Chemical formula 4]

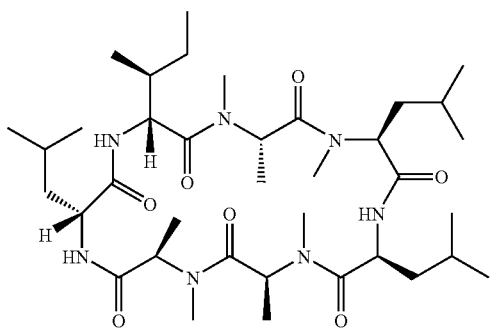

[Chemical formula 5]

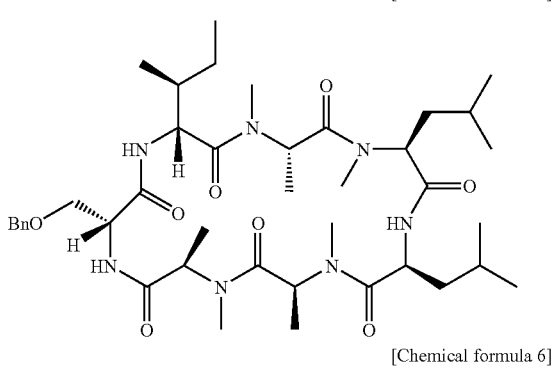

[Chemical formula 6]

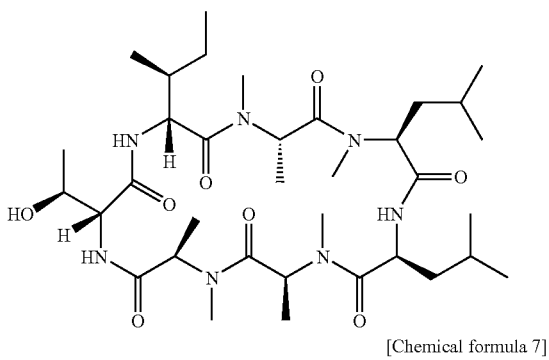

[Chemical formula 7]

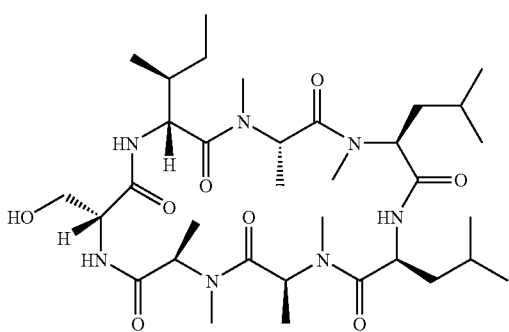

A study conducted by the present inventors revealed that all of the cyclic heptapeptides described above exhibited a preadipocyte differentiation-inhibitory effect or an adipocyte fat accumulation-inhibitory effect (for the sake of convenience, these two effects are collectively called "the effects of the present invention" hereinbelow). Furthermore, it was also revealed that all of the cyclic heptapeptides described above were less cytotoxic than ternatin, which is a practical advantage.

The amino acid at the 7-position of ternatin is β-OH-D-Leu. It is difficult to synthesize this amino acid because it has a hydroxyl group. Therefore, since it is difficult to synthesize an amino acid with a hydroxyl group through six steps in a conformationally-constrained fashion, it is difficult to synthesize ternatin. In the cyclic heptapeptide of the present invention, the amino acid has been replaced by another easily accessible amino acid; hence, it is easier to synthesize the cyclic heptapeptides than ternatin.

As shown above, the cyclic heptapeptide of the present invention is more potent than ternatin in many respects No particular limitation is imposed on the method for the synthesis of the cyclic heptapeptide (production method) of the present invention. For example, the cyclic heptapeptide of the present invention can be obtained by a synthesis method described later in the Examples. In the synthesis method, a desired cyclic heptapeptide can be obtained by amide bond formation and subsequent macrolactamization via certain tripeptides and tetrapeptides as intermediates. According to the method, a related compound with a modified constituent amino acid can be obtained with ease and in high yield.

The cyclic heptapeptide of the present invention can be used as a preadipocyte differentiation-inhibitory agent or an adipocyte fat accumulation-inhibitory agent, either alone or with other ingredient(s). The cyclic heptapeptide of the present invention can be used not only for medical and cosmetic purposes, but also for research purposes such as in studies on molecular mechanisms and fat-accumulation mechanisms in adipocytes, or for the purpose of developing an anti-obesity medicine (medicine for treatment or prophylaxis of obesity), a weight-loss medicine, and the like.

In another aspect of the present invention, a compound containing the cyclic heptapeptide of the present invention as an active ingredient is provided. Although no particular limitation is imposed on the use of the compound of the present invention, it is preferably used for a medicine, food, or cosmetic agent. Thus, as a preferable embodiment, the present invention provides a pharmaceutical composition, a food composition, and a cosmetic composition containing the cyclic heptapeptide of the present invention as an active ingredient. Two or more of the present cyclic heptapeptides can be used in combination.

The pharmaceutical composition of the present invention is potentially used as an anti-obesity medicine. The term "obesity" as used herein generally refers to a condition in which fat tissue is excessively accumulated in the body. In the present specification, the term "obesity" is broadly interpreted, and adiposity is included in concept thereof. "Adiposity" refers to a pathological condition that medically requires weight loss, and accompanies, or, is predicted to accompany in the future, a health problem (complication) caused by or associated with obesity.

An example of a method for the assessment of obesity includes one that employs the widely used BMI (body mass index) as a scale. BMI is obtained by dividing the weight (kg) by the square of the height (m) (BMI=weight (kg)/height $(m)^2$). Assessment is provided as follows; BMI<18.5 is underweight (underweight), 18.5≦BMI<25 is normal weight (normal range), 25≦BMI<30 is obese stage 1 (preobese), 30≦BMI<35 is obese stage 2 (obese class I), 35≦BMI<40 is obese stage 3 (obese class II), and 40<BMI is obese stage 4 (obese class III), where the assessment in parentheses is provided by WHO. In another assessment method which uses BMI, the standard weight of Japanese adults (ideal weight) is calculated using the following formula; the standard weight (kg)=height $(m)^2 \times 22$, and the condition in which the actual weight is more than 120% of the standard weight (calculated value) is considered to be obesity. Nevertheless, because the standard weight (ideal weight) varies depending on the individual due to differences in sex, age, or lifestyle, it is unreasonable to apply the above assessment uniformly for the assessment of obesity.

The pharmaceutical composition of the present invention can be prepared according to an ordinary method. The pharmaceutical composition can also contain other ingredient(s) that are acceptable for use in a pharmaceutical preparation (such as a carrier, an excipient, a disintegrant, a buffer, an emulsifier, a suspension agent, a pain-killing agent, a stabilizer, a preservative, an antiseptic agent, and physiological saline). As an excipient, lactose, starch, sorbitol, D-mannitol, sucrose, and the like can be used. As a disintegrant, starch, carboxymethylcellulose, calcium carbonate, and the like can be used. As a buffer, phosphate, citrate, acetate, and the like can be used. As an emulsifier, gum arabic, sodium alginate, tragacanth, and the like can be used. As a suspension agent, glyceryl monostearate, aluminum monostearate, methylcellulose, carboxymethylcellulose, hydroxymethylcellulose, sodium lauryl sulfate, and the like can be used. As a pain-killing agent, benzyl alcohol, chlorobutanol, sorbitol, and the like can be used. As a stabilizer, propylene glycol, ascorbic acid, and the like can be used. As a preservative, phenol, benzalkonium chloride, benzyl alcohol, chlorobutanol, methylparaben, and the like can be used. As an antiseptic agent, benzalkonium chloride, parahydroxybenzoate, chlorobutanol, and the like can be used.

No particular limitation is imposed on the dosage form in preparation of the pharmaceutical composition, and the medicine of the present invention can be provided as, for example, a tablet, a powder, a fine-granule, a granule, a capsule, a syrup, an injection, an external agent, or a suppository.

The pharmaceutical composition of the present invention contains an amount necessary to obtain an expected therapeutic effect (including prophylactic effect), i.e., a therapeutically effective amount, of an active ingredient. Although the amount of the active ingredient in the pharmaceutical composition of the present invention generally varies depending on the dosage form, it can be set, for example, within a range of approximately 0.1 wt. % to approximately 95 wt. % to achieve a desired dosage.

The pharmaceutical composition of the present invention can be given to a subject by oral or parenteral administration (intravenous, intra-arterial, subcutaneous, intramuscular, or intraperitoneal injection, or percutaneous, nasal, or mucosal administration, and the like) according to the dosage form. No particular limitation is imposed on the "subject" used herein, and includes humans and other animals (including a pet animal, livestock, and an experimental animal. Specific examples thereof include a mouse, a rat, a guinea pig, a hamster, a monkey, a cow, a pig, a goat, a sheep, a dog, a cat, a chicken, and a quail). In a preferable embodiment, the medicine of the present invention is given to a human.

The dosage of the pharmaceutical composition of the present invention is set so as to achieve an expected therapeutic effect. Generally, the symptoms, age, sex, and weight of the patient, and the like are taken into consideration for setting a therapeutically effective dosage. A person who is skilled in the art can set an appropriate dosage based on a consideration of the above parameters. For example, the dosage for an adult (weight of approximately 60 kg) can be set so that the daily dose of the active ingredient is approximately 1 mg to approximately 6 g, preferably approximately 6 mg to approximately 600 mg. As an administration schedule, for example, once to several times daily, once every other day, or once every three days, and the like, can be adopted. In preparation of an administration schedule, the pathological condition of the patient, duration of effectiveness of the active ingredient, and the like, should be taken into consideration.

As described above, an embodiment of the present invention is a food composition that contains the cyclic heptapeptide of the present invention as an active ingredient. Examples of the "food composition" in the present invention include general food (grain, vegetable, meat, various processed food, snack, milk, soft drink, alcoholic beverage, and the like), nutritional supplement food (supplement, energy drink, and the like), and a food additive. In the case of a nutritional supplement food or a food additive, the cyclic heptapeptide of the present invention can be provided in the form of a powder, granule, tablet, paste, liquid, and the like. Provision of the cyclic heptapeptide of the present invention in the form of a food composition enables daily intake as well as continuous intake of the cyclic heptapeptide of the present invention.

It is preferable that the active ingredient is contained in the food composition of the present invention at such an amount that a therapeutic or prophylactic effect can be expected. The amount added can be decided upon based on a consideration of the pathological condition, health, age, sex, weight, and the like of the subject to be administered the food composition of the present invention.

As described above, an embodiment of the present invention is a cosmetic composition that contains the cyclic heptapeptide of the present invention as an active ingredient.

The cosmetic composition of the present invention can be obtained by mixing the cyclic heptapeptide of the present invention with ingredients and base materials that are normally used in a cosmetic agent (for example, various fat and oil, mineral oil, vaseline, squalane, lanolin, beeswax, denatured alcohol, dextrin palmitate, glycerin, a glycerin fatty acid ester, ethylene glycol, paraben, camphor, menthol, various vitamins, zinc oxide, titanium oxide, benzoic acid, edetic acid, chamomile oil, carrageenan, chitin powder, chitosan, perfume, colorant, and the like).

The cosmetic composition can be provided in the form of, for example, an emulsion for the face or body, a toner, a cream, a lotion, an essence, oil, a pack, a sheet, and a cleansing agent. No particular limitation is imposed on the amount of the cyclic heptapeptide contained in the cosmetic composition.

For example, the cyclic heptapeptide can be added at 0.1 wt. % to 60 wt. %.

EXAMPLES

1. Synthesis Method of the Novel Cyclic Heptapeptide

A method including a series of reactions as shown below was proposed as a method for synthesizing a desired cyclic heptapeptide.

[Chemical formula 8]

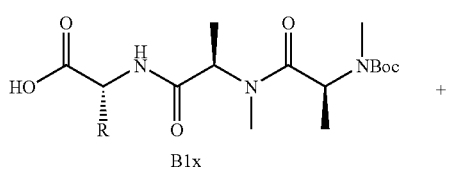

B1x

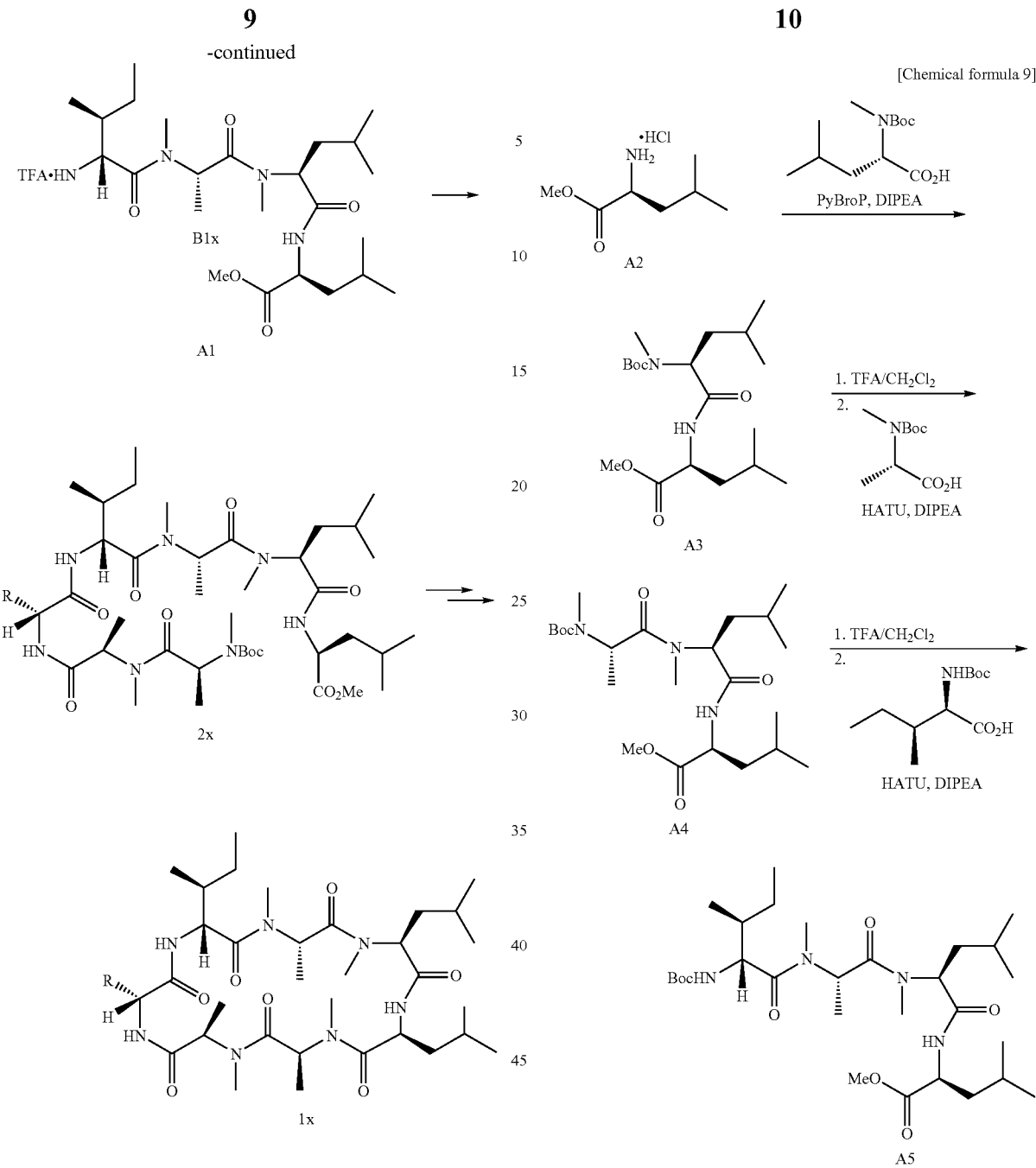

According to the above synthesis method, a desired cyclic heptapeptide (such as a related compound in which a constituent amino acid in ternatin is modified) can be obtained with ease and at a high-yield by amide bond formation and subsequent macrolactamization via certain tripeptides (B1x) and tetrapeptides (A1) as intermediates.

2. Synthesis of the Novel Cyclic Heptapeptide

Various cyclic heptapeptides were synthesized by the novel synthesis method shown in the above 1.

(1) Synthesis of Tetrapeptide Intermediates (A1)

Following a series of reactions shown below, Boc-tetrapeptides A5, in which a terminal amino acid is protected with a t-butoxycarbonyl group (Boc), was synthesized. Tetrapeptide intermediates (A1) were obtained by treating A5 with an acid (TFA) before use.

Under a nitrogen atmosphere, 91 mg (0.50 mmol) of L-Leu-OMe.HCl (A2), 123 mg (0.50 mmol) of Boc-NMe-L-Leu-OH, and 256 mg (0.55 mmol) of PyBroP were dissolved in 1 mL of dichloromethane, and the mixture was cooled to 0° C. After addition of 260 μL (1.50 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (5 mL×3), and then combined organic layers were washed with saturated sodium bicarbonate solution (3 mL) and saturated saline (5 mL×2), and then dried over anhydrous sodium sulfate. The resulting solution was concentrated under reduced pressure, and the oily substance obtained thereby was purified by column chromatography (silica gel, hexane-ether 2/1) to yield 149 mg (80%) of colorless solid dipeptides A3.

The dipeptides A3 thus obtained (105 mg, 0.28 mmol) were dissolved in 1 mL of dichloromethane under a nitrogen atmosphere, and the mixture was cooled to 0° C. TFA (1 mL) was added to this reaction solution, followed by stirring for two hours. The reaction mixture thus obtained was concentrated under reduced pressure and then subjected to azeotropic distillation with toluene three times to give a light yellow oily substance. The oily substance thus obtained, 57 mg (0.28 mmol) of Boc-NMe-L-Ala-OH, and 118 mg (0.31 mmol) of HATU were dissolved in 1 mL of dichloromethane and 0.4 mL of DMF, and the resulting mixture was cooled to 0° C. After addition of 147 µL (0.85 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (3 mL×3), and then combined organic layers were washed with saturated sodium bicarbonate solution (3 mL) and saturated saline (3 mL×2), and then dried over anhydrous sodium sulfate. The resulting solution was concentrated under reduced pressure, and the oily substance obtained thereby was purified by column chromatography (silica gel, hexane-ether 2/1→1/1) to yield 104 mg (81%) of colorless oily tripeptides A4.

The tripeptides A4 thus obtained (104 mg, 0.23 mmol) were dissolved in 1 mL of dichloromethane under a nitrogen atmosphere, and the mixture was cooled to 0° C. TFA (1 mL) was added to this reaction solution, followed by stirring for two hours. The reaction mixture thus obtained was concentrated under reduced pressure and then subjected to azeotropic distillation with toluene three times to give a light yellow oily substance. The oily substance thus obtained, 57 mg (0.23 mmol) of Boc-D-allo-Ile-OH.1/2H$_2$O that had been subjected to azeotropic distillation with toluene, 95 mg (0.25 mmol) of HATU were dissolved in 1 mL of dichloromethane and 0.2 mL of DMF, and the resulting mixture was cooled to 0° C. After addition of 119 µL (0.68 mmol) of diisopropylethylamine, the mixture was brought back to room temperature, followed by stirring for four hours. The reaction was stopped by addition of 0.12 M hydrochloric acid. The reaction mixture thus obtained was extracted with ethyl acetate (3 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 2/1→1/1→0/1) to yield 113 mg (87%) of colorless oily Boc-tetrapeptide A5.

(2) Synthesis of Tripeptide Intermediate Ethyl Esters B4

Following a series of reactions shown below, tripeptides B4 were synthesized. Tripeptide intermediates (B1) were obtained by alkaline hydrolysis of B4 before use.

[Chemical formula 10]

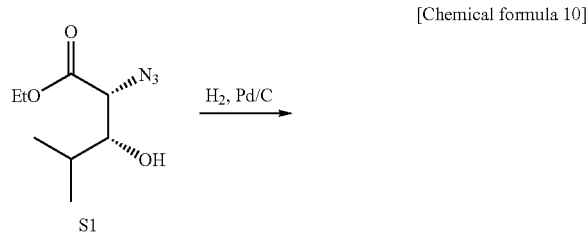

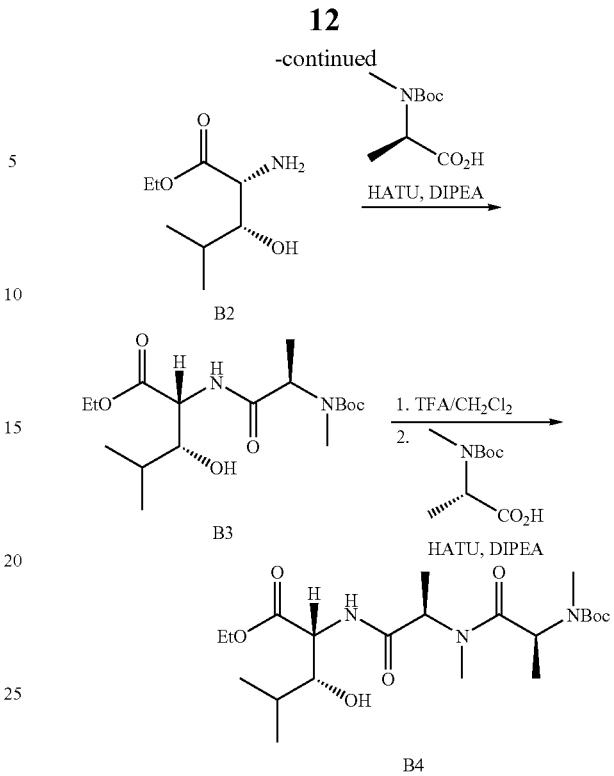

Under a nitrogen atmosphere, azide compounds S1 (400 mg, 2.0 mmol), which had been synthesized in accordance with literature (Hale, K. J.; Manaviazar, S.; Delisser, V. M. Tetrahedron 1994, 50, 9181-9188), and 40 mg of 5% Pd/C were dissolved in 5 mL of methanol. The atmosphere in the above reaction system was replaced with hydrogen gas, followed by stirring for 14 hours. Then, the resulting reaction mixture was filtrated through Celite, and the filtrate thus obtained was concentrated under reduced pressure to yield 359 mg (100%) of light yellow β-OH-D-Leu ethyl esters B2. Under a nitrogen atmosphere, B2 thus obtained (87 mg, 0.50 mmol), 102 mg (0.50 mmol) of Boc-NMe-D-Ala-OH, 256 mg (0.55 mmol) of PyBroP were dissolved in 1 mL of dichloromethane, and the mixture was cooled to 0° C. After addition of 260 µL (1.50 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate.

The resulting solution was concentrated under reduced pressure, and the oily substance obtained thereby was purified by column chromatography (silica gel, hexane-ether 2/1→1/1) to yield 150 mg (83%) of colorless solid dipeptides B3.

The dipeptides B3 thus obtained (125 mg, 0.35 mmol) were dissolved in 1 mL of dichloromethane under a nitrogen atmosphere, and the mixture was cooled to 0° C. TFA (1 mL) was added to this reaction solution, followed by stirring for two hours. The reaction mixture thus obtained was concentrated under reduced pressure and then subjected to azeotropic distillation with toluene three times to give a colorless oily substance. The oily substance thus obtained, 70 mg (0.35 mmol) of Boc-NMe-L-Ala-OH, and 145 mg (0.38 mmol) of HATU were dissolved in 1 mL of dichloromethane and 0.4 mL of DMF, and the resulting mixture was cooled to 0° C.

After addition of 181 μL (1.0 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (3 mL×3), and then combined organic layers were washed with saturated sodium bicarbonate solution (3 mL) and saturated saline (3 mL×2), and then dried over anhydrous sodium sulfate. The resulting solution was concentrated under reduced pressure, and the oily substance obtained thereby was purified by column chromatography (silica gel, hexane-ether 1/2→0/1) to yield 93 mg (60%) of colorless oily tripeptide intermediate ethyl esters B4.

(3) Synthesis of Ternatin

Following a series of reactions shown below, ternatin was synthesized.

[Chemical formula 11]

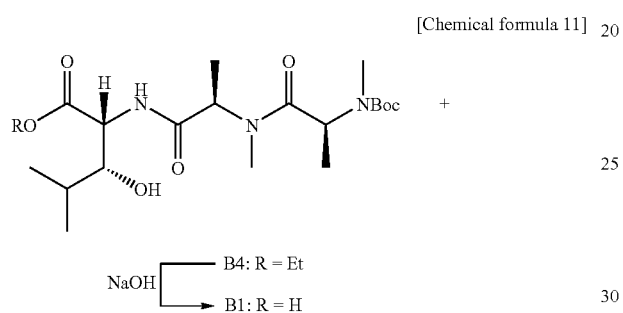

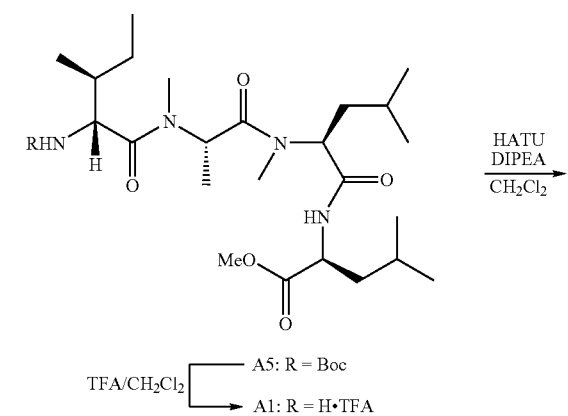

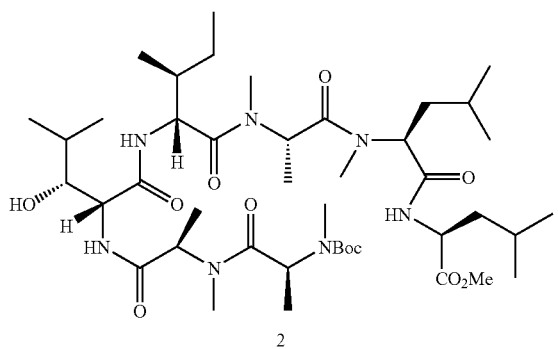

[Chemical formula 12]

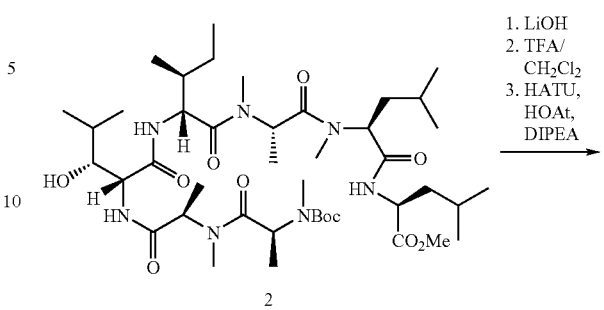

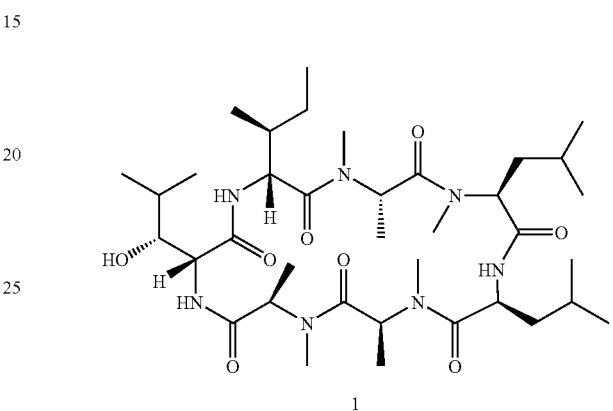

The tripeptide intermediate ethyl esters B4 obtained in the above (2) (69 mg, 0.16 mmol) were dissolved in 1,4-dioxane, and the mixture was cooled to 0° C. To this reaction solution, 0.5 mL of 1 M sodium hydroxide solution was added, followed by stirring for two hours. The reaction mixture thus obtained was made acidic (<pH 3) with addition of 0.12 M hydrochloric acid, followed by extraction with ethyl acetate (5 mL×4), and then combined organic layers were dried over anhydrous sodium sulfate. The resulting solution was concentrated under reduced pressure to yield 54 mg (84%) of tripeptide intermediates B1. Under a nitrogen atmosphere, the Boc-tetrapeptides A5 (51 mg, 0.089 mmol) were dissolved in 1 mL of dichloromethane, and the mixture was cooled to 0° C. TFA (1 mL) was added to this reaction solution, followed by stirring for two hours. The reaction mixture thus obtained was concentrated under reduced pressure and then subjected to azeotropic distillation with toluene three times to give colorless oily tetrapeptide intermediates A1.

Under a nitrogen atmosphere, A1 and B1 were dissolved in 0.5 mL of dichloromethane and 0.1 mL of DMF, and the mixture was cooled to 0° C. After addition of 46 μL (0.27 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 1/1→0/1→ether-ethyl acetate 1/1→) to yield 68 mg (88%) of colorless solid heptapeptides 2.

The heptapeptides 2 thus obtained (4.1 mg, 4.7 μmol) were dissolved in 0.1 mL of THF, 0.1 mL of water, and 0.4 mL of t-BuOH. To this mixture, 2.0 mg (47 μmol) of lithium hydroxide monohydrate was added, followed by stirring for one and half hours. The reaction mixture thus obtained was made acidic (<pH 3) with addition of 0.12 M hydrochloric acid, followed by extraction with ethyl acetate (5 mL×3), and then combined organic layers were dried over anhydrous sodium sulfate. The resulting solution was concentrated under reduced pressure to yield carboxylic acid.

Under a nitrogen atmosphere, the carboxylic acid thus obtained was dissolved in 0.5 mL of dichloromethane, and the mixture was cooled to 0° C. TFA (0.1 mL) was added to this reaction solution, followed by stirring for one and half hours. The reaction mixture thus obtained was concentrated under reduced pressure and then subjected to azeotropic distillation with toluene three times to give colorless oily cyclization precursors.

Under a nitrogen atmosphere, the cyclization precursors thus obtained, 3.6 mg (9.4 μmol) of HATU, and 1.3 mg (9.4 mmol) of HOAt were dissolved in 3.0 mL of dichloromethane and 0.1 mL of DMF, and the mixture was cooled to 0° C. After addition of 3.7 μL (21 μmol) of diisopropylethylamine, the mixture was stirred at 0° C. for one hour. Subsequently, the mixture was brought back to room temperature, followed by stirring for twelve hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, chloroform-methanol 1/0→39/1→) to yield 3.5 mg (100%, three steps) of colorless solid ternatin (1). FIG. 1 shows $^1$H NMR spectrum of 1 obtained as above.

Ternatin (1): $^1$H NMR (800 MHz, C$_6$D$_6$)δ7.95 (d, J=9.2 Hz, 1 H), 7.59 (d, J=8.7 Hz, 1 H), 6.23 (d, J=6.4 Hz, 1 H), 5.89 (d, J=2.7 Hz, 1H), 5.69 (q, J=6.9 Hz, 1 H), 5.66 (q, J=6.9 Hz, 1 H), 5.20 (td, J=8.0, 2.0 Hz, 1 H), 5.17 (dd, 1 H), 4.48 (dd, J=6.9, 3.2 Hz, 1 H), 4.31 (dd, J=10.1, 4.0 Hz, 1 H), 3.98 (dd, J=9.4, 2.1 Hz, 1 H), 3.30 (s, 3 H), 2.79 (s, 3 H), 2.68 (s, 3 H), 2.60 (s, 3 H), 2.36 (m, 1H), 2.23 (m, 1 H), 2.12 (m, 1 H), 1.73-1.84 (m, 2 H), 1.64 (m, 1 H), 1.54 (d, J=6.4 Hz, 3 H), 1.45 (d, J=6.9 Hz, 3 H), 1.27 (d, J=7.3 Hz, 3 H), 1.25 (m, 1 H), 1.25 (d, J=6.9 Hz, 3 H), 1.18 (d, J=6.9 Hz, 3 H), 1.01 (ddd, J=13.3, 9.4, 4.1 Hz, 1 H), 0.97 (d, J=6.4 Hz, 3 H), 0.93 (d, J=6.9 Hz, 3 H), 0.90 (d, J=6.9 Hz, 3 H), 0.90 (m, 1 H), 0.79 (m, 1 H), 0.75 (d, J=7.3 Hz, 3 H), 0.60 (d, J=6.9 Hz, 3 H), 0.57 (t, J=7.4 Hz, 3 H);

$^{13}$C NMR (201 MHz, C$_6$D$_6$)δ174.6, 174.5, 174.2, 172.7, 169.9, 168.8 (2 C), 76.0, 59.2, 56.3, 55.1, 52.3, 51.3, 49.8 (2 C), 40.5, 37.9, 33.7, 30.7, 30.2, 29.7, 29.4 (2C), 26.7, 26.0, 25.3, 23.9, 23.3, 22.6, 21.3 (2C), 15.9, 14.8, 14.2, 13.6, 13.1, 11.6;

HRMS (FAB) calcd for C$_{37}$H$_{67}$N$_7$O$_8$Na (M+Na)$^+$ 760.4949, found 760.4922.

(4) Synthesis of B4a

Following a series of reactions shown below, tripeptide intermediate methyl esters B4a were synthesized. Tripeptide intermediates (B1a) were obtained by alkaline hydrolysis of B4a before use.

[Chemical formula 13]

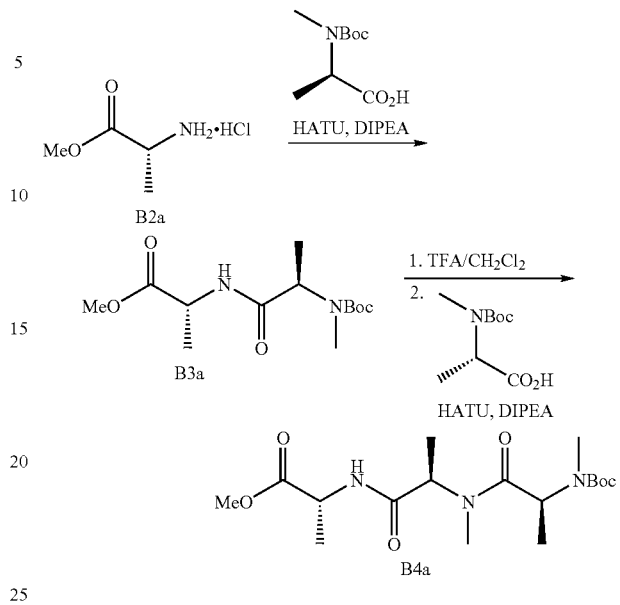

Under a nitrogen atmosphere, 180 mg (1.3 mmol) of D-Ala-OMe.HCl (B2a), 262 mg (1.3 mmol) of Boc-NMe-D-Ala-OH, 662 mg (1.4 mmol) of PyBroP were dissolved in 2.5 mL of dichloromethane, and the mixture was cooled to 0° C. After addition of 674 μL (3.9 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 2/1→1/1) to yield 306 mg (82%) of colorless solid dipeptides B3a.

The dipeptides B3a thus obtained (209 mg, 0.72 mmol) were dissolved in 1 mL of dichloromethane under a nitrogen atmosphere, and the mixture was cooled to 0° C. TFA (1 mL) was added to this reaction solution, followed by stirring for two hours. The reaction mixture thus obtained was concentrated under reduced pressure and then subjected to azeotropic distillation with toluene three times to give a colorless oily substance. The oily substance thus obtained, 146 mg (0.72 mmol) of Boc-NMe-L-Ala-OH, 301 mg (0.79 mmol) of HATU were dissolved in 1.3 mL of dichloromethane and 0.2 mL of DMF, and the resulting mixture was cooled to 0° C. After addition of 376 μL (2.2 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (3 mL×3), and then combined organic layers were washed with saturated sodium bicarbonate solution (3 mL) and saturated saline (3 mL×2), and then dried over anhydrous sodium sulfate. The resulting solution was concentrated under reduced pressure, and the oily substance obtained thereby was purified by column chromatography (silica gel, hexane-ether 1/1→1/2→0/1) to yield 140 mg (52%) of colorless oily tripeptides B4a.

(5) Synthesis of Cyclic Heptapeptides (1a)

Following a series of reactions shown below, cyclic heptapeptides (1a) were synthesized.

[Chemical formula 14]

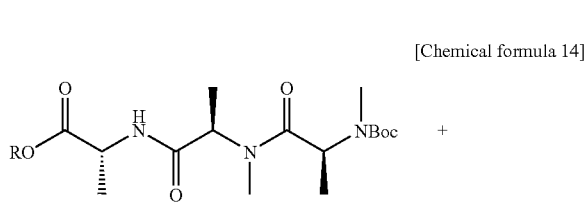

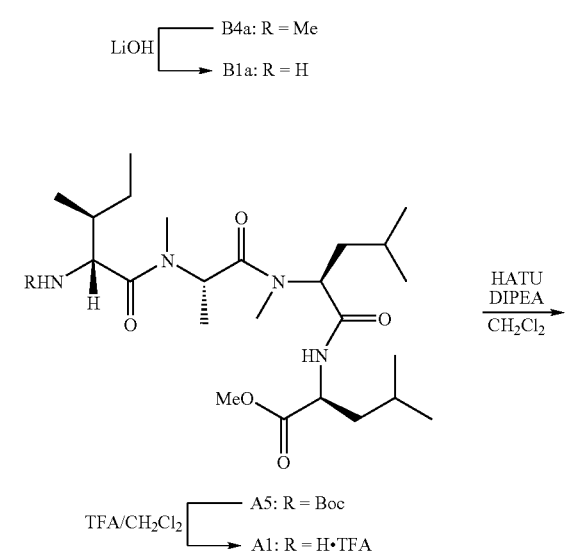

[Chemical formula 15]

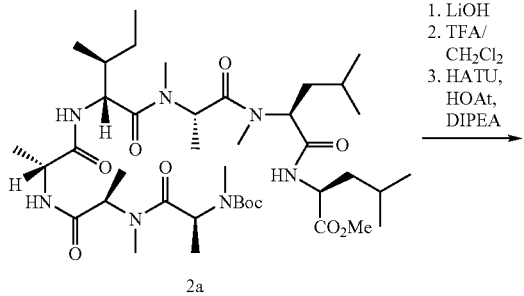

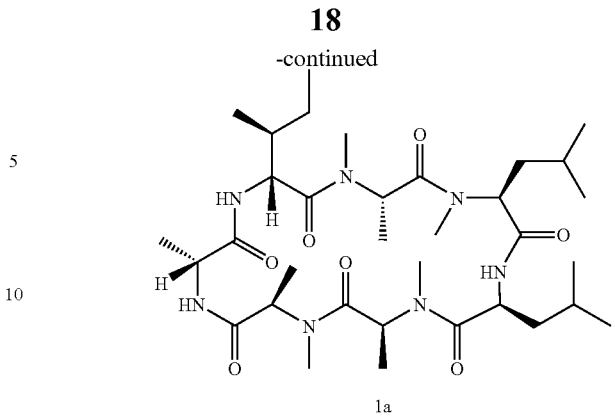

The tripeptides B4a obtained in the above (4) (38 mg, 0.10 mmol) were dissolved in 0.5 mL of THF, 0.5 mL of water, and 2.0 mL of t-BuOH. To this mixture, 21 mg (0.50 mmol) of lithium hydroxide monohydrate was added, followed by stirring for two hours. The reaction mixture thus obtained was made acidic (<pH 3) with addition of 0.12 M hydrochloric acid, followed by extraction with ethyl acetate (5 mL×3), and then combined organic layers were dried over anhydrous sodium sulfate. The resulting solution was concentrated under reduced pressure to yield tripeptide intermediates B1a.

The Boc-tetrapeptides A5 (55 mg, 96% mol) were dissolved in 0.5 mL of dichloromethane under a nitrogen atmosphere, and the mixture was cooled to 0° C. TFA (0.5 mL) was added to this reaction solution, followed by stirring for two hours. The reaction mixture thus obtained was concentrated under reduced pressure and then subjected to azeotropic distillation with toluene three times to give colorless oily tetrapeptide intermediates A1. Under a nitrogen atmosphere, A1, B1a, 40 mg (0.10 mmol) of HATU were dissolved in 0.5 mL of dichloromethane and 0.1 mL of DMF, and the resulting mixture was cooled to 0° C. After addition of 50 μL (0.29 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 1/1→1/2→0/1→ether-ethyl acetate 9/1→4/1) to yield 81 mg (100%) of colorless solid heptapeptides 2a.

The heptapeptides 2a thus obtained (48 mg, 59 μmol) were dissolved in 0.25 mL of THF, 0.25 mL of water, and 1.0 mL of t-BuOH. To this mixture, 12 mg (0.30 mmol) of lithium hydroxide monohydrate was added, followed by stirring for two and half hours. The reaction mixture thus obtained was made acidic (<pH 3) with addition of 0.12 M hydrochloric acid, followed by extraction with ethyl acetate (5 mL×3), and then combined organic layers were dried over anhydrous sodium sulfate. The resulting solution was concentrated under reduced pressure to yield carboxylic acid. Under a nitrogen atmosphere, the carboxylic acid thus obtained was dissolved in 0.5 mL of dichloromethane, and the mixture was cooled to 0° C. TFA (0.5 mL) was added to this reaction solution, followed by stirring for one and half hours. The reaction mixture thus obtained was concentrated under reduced pressure and then subjected to azeotropic distillation with toluene three times to give colorless oily cyclization precursors.

Figure 2:
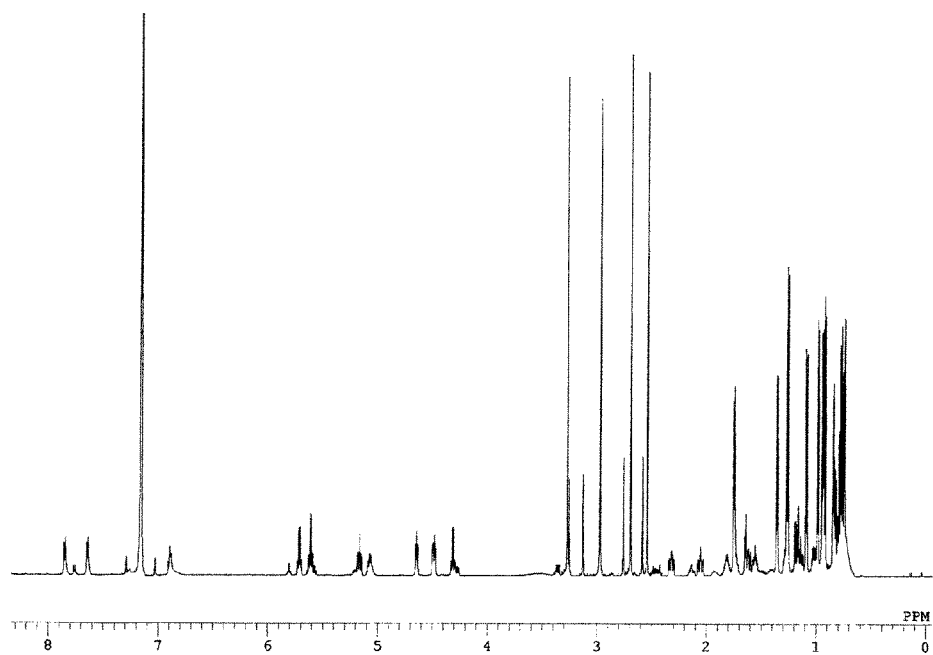
FIG. 2 is a $^1H$ NMR spectrum of cyclic heptapeptide (1a) ($C_6D_6$, 600 MHz).

Under a nitrogen atmosphere, the cyclization precursors thus obtained, 45 mg (0.12 mmol) of HATU, and 16 mg (0.12 mmol) of HOAt were dissolved in 39 mL of dichloromethane and 0.5 mL of DMF, and the mixture was cooled to 0° C. After addition of 46 µL (0.27 mmol) of diisopropylethylamine, the mixture was brought back to room temperature, followed by stirring for 46 hours. The reaction was stopped by addition of 0.12 M hydrochloric acid. The reaction mixture thus obtained was extracted with ethyl acetate (100 mL), and then combined organic layers were washed with saturated sodium bicarbonate solution (15 mL) and saturated saline (15 mL×2), and then dried over anhydrous sodium sulfate. The resulting solution was concentrated under reduced pressure, and the oily substance obtained thereby was purified by column chromatography (silica gel, chloroform-methanol 1/0→39/1→) to yield 43 mg of partially purified products. The partially purified products thus obtained were purified by reverse-phase high performance liquid chromatography [Develosil ODS HG-5 (diameter of 20×250 mm), 50% acetonitrile at a flow rate of 5 mL/min, UV at 215 nm] to yield 24 mg (60%, three steps) of cyclic heptapeptides (1a). FIG. 2 shows $^1$H NMR spectrum of 1a obtained as above.

(1a):major conformer, $^1$H NMR (600 MHz, $C_6D_6$) δ7.85 (d, J=8.8 Hz, 1 H), 7.64 (d, J=8.8 Hz, 1 H), 6.89 (br d, 1 H), 5.71 (q, J=6.6 Hz, 1 H), 5.61 (q, J=7.3 Hz, 1 H), 5.17 (m, 1 H), 5.07 (m, 1 H), 4.65 (t, J=5.5 Hz, 1 H), 4.48 (m, 1 H), 4.31 (q, J=7.3 Hz, 1 H), 3.27 (s, 3 H), 2.98 (s, 3 H), 2.70 (s, 3 H), 2.54 (s, 3 H), 2.32 (m, 1 H), 2.06 (m, 1 H), 1.81 (m, 1 H), 1.75 (d, J=7.0 Hz, 3 H), 1.62 (m, 1 H), 1.56 (m, 1 H), 1.36 (d, J=6.6 Hz, 3 H), 1.32-0.75 (m, 4 H), 1.27 (d, J=7.3 Hz, 3 H), 1.09 (d, J=6.6 Hz, 3 H), 0.99 (d, J=6.6 Hz, 3 H), 0.95 (d, J=7.0 Hz, 3 H), 0.93 (d, J=6.6 Hz, 3 H), 0.85 (d, J=6.6 Hz, 3 H), 0.78 (t, J=7.4 Hz, 3 H), 0.77 (d, J=7.3 Hz, 3 H);

$^{13}$C NMR (150 MHz, $C_6D_6$)δ174.8, 174.1, 173.7, 171.5, 169.9, 169.8, 169.4, 58.9, 53.7, 51.8, 51.4, 49.9, 49.7, 48.9, 40.2, 38.7, 35.7, 30.7, 29.8, 29.7, 29.6, 26.4, 25.8, 25.2, 23.8, 23.4, 22.6, 21.4, 20.0, 15.7, 14.6, 13.8, 13.3, 11.9.

(6) Synthesis of B4b

Following a series of reactions shown below, tripeptide intermediate methyl esters B4b were synthesized. Tripeptide intermediates (B1b) were obtained by alkaline hydrolysis of B4b before use.

[Chemical formula 16]

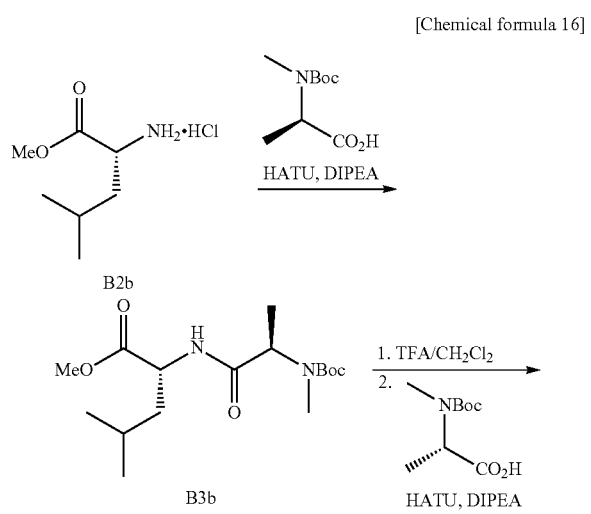

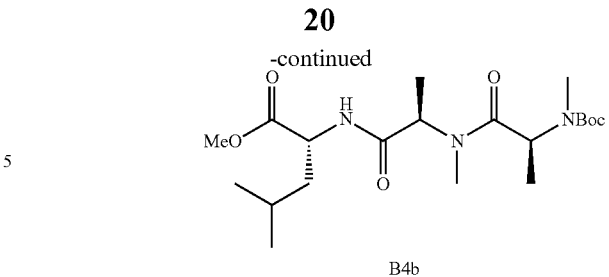

B4b

Under a nitrogen atmosphere, 250 mg (1.4 mmol) of D-Leu-OMe.HCl (B2b), 262 mg (1.4 mmol) of Boc-NMe-D-Ala-OH, and 577 mg (1.5 mmol) of HATU were dissolved in 2.5 mL of dichloromethane and 0.2 mL of DMF, and the mixture was cooled to 0° C. After addition of 1.35 µL (7.74 mmol) of diisopropylethylamine, the mixture was brought back to room temperature, followed by stirring for three hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 1/2) to yield 350 mg (77%) of colorless solid dipeptides B3b.

The dipeptides B3b thus obtained (210 mg, 0.64 mmol) were dissolved in 1 mL of dichloromethane under a nitrogen atmosphere, and the mixture was cooled to 0° C. TFA (1 mL) was added to this reaction solution, followed by stirring for one and half hours. The reaction mixture thus obtained was concentrated under reduced pressure and then subjected to azeotropic distillation with toluene three times to give a colorless oily substance. The oily substance thus obtained, 185 mg (0.91 mmol) of Boc-NMe-L-Ala-OH, and 380 mg (1.0 mmol) of HATU were dissolved in 1.5 mL of dichloromethane and 0.2 mL of DMF, and the resulting mixture was cooled to 0° C. After addition of 475 µL (2.7 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 2/1→1/1→0/1) to yield 227 mg (85%) of colorless oily tripeptides Bob.

(7) Synthesis of Cyclic Heptapeptides (1b)

Following a series of reactions shown below, cyclic heptapeptides (1b) was synthesized.

[Chemical formula 17]

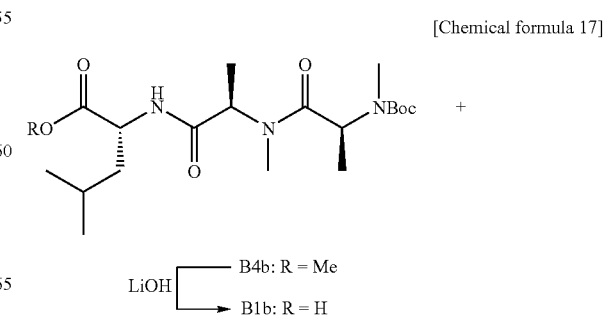

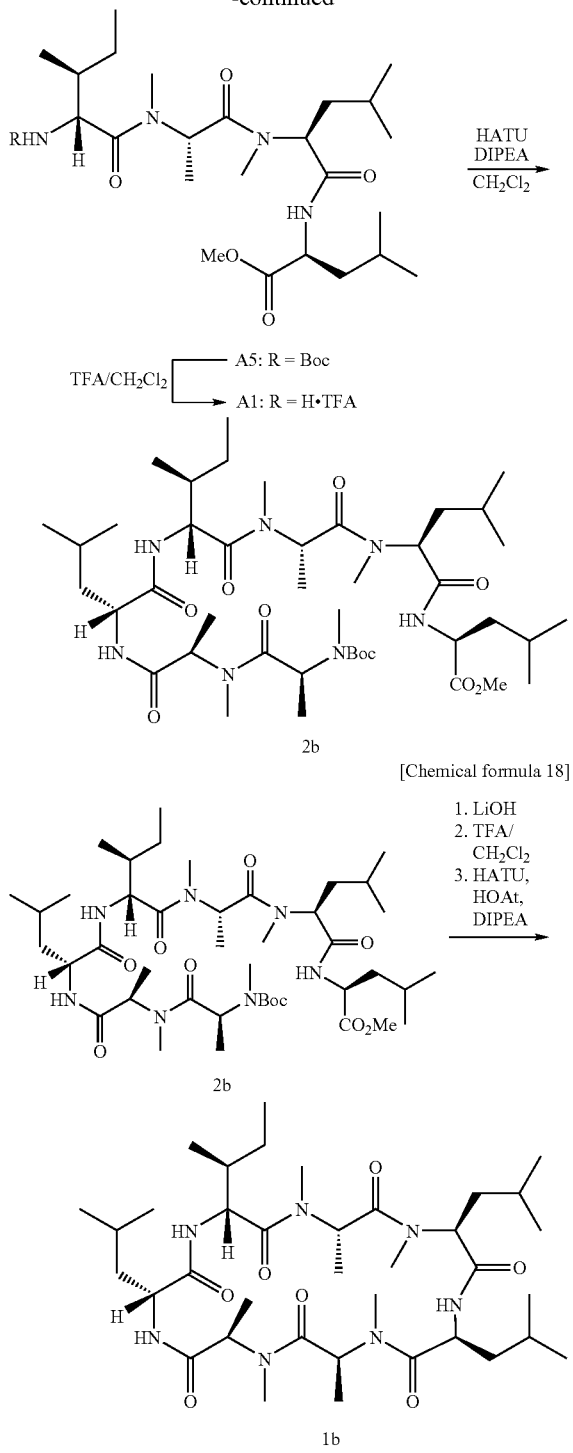

The tripeptides B4b obtained in the above (6) (40 mg, 0.10 mmol) were dissolved in 0.5 mL of THF, 0.5 mL of water, and 2.0 mL of t-BuOH. To this mixture, 20 mg (0.48 mmol) of lithium hydroxide monohydrate was added, followed by stirring for two hours. The reaction mixture thus obtained was made acidic (<pH 3) with addition of 0.12 M hydrochloric acid, followed by extraction with ethyl acetate (5 mL×3), and then combined organic layers were dried over anhydrous sodium sulfate. The resulting solution was concentrated under reduced pressure to yield tripeptide intermediates B1b.

The Boc-tetrapeptides A5 (55 mg, 96% mol) were dissolved in 0.5 mL of dichloromethane under a nitrogen atmosphere, and the mixture was cooled to 0° C. TFA (0.5 mL) was added to this reaction solution, followed by stirring for two hours. The reaction mixture thus obtained was concentrated under reduced pressure and then subjected to azeotropic distillation with toluene three times to give colorless oily tetrapeptide intermediates A1. A1, B1b, and 40 mg (0.10 mmol) of HATU were dissolved in 0.5 mL of dichloromethane and 0.1 mL of DMF, and the resulting mixture was cooled to 0° C. After addition of 50 μL (0.29 mmol) of diisopropylethylamine, the mixture was brought back to room temperature, followed by stirring for three hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 1/1→2/1→0/1→ether-ethyl acetate 9/1→) to yield 57 mg (70%) of colorless pasty heptapeptides 2b.

The heptapeptides 2b thus obtained (46 mg, 54 μmol) was dissolved in 0.25 mL of THF, 0.25 mL of water, and 1.0 mL of t-BuOH. To this mixture, 11 mg (0.27 mmol) of lithium hydroxide monohydrate was added, followed by stirring for two and half hours. The reaction mixture thus obtained was made acidic (<pH 3) with addition of 0.12 M hydrochloric acid, followed by extraction with ethyl acetate (5 mL×3), and then combined organic layers were dried over anhydrous sodium sulfate. The resulting solution was concentrated under reduced pressure to yield carboxylic acid. Under a nitrogen atmosphere, the carboxylic acid thus obtained was dissolved in 0.5 mL of dichloromethane, and the mixture was cooled to 0° C. TFA (0.5 mL) was added to this reaction solution, followed by stirring for one and half hours. The reaction mixture thus obtained was concentrated under reduced pressure and then subjected to azeotropic distillation with toluene three times to give colorless oily cyclization precursors.

Figure 3:
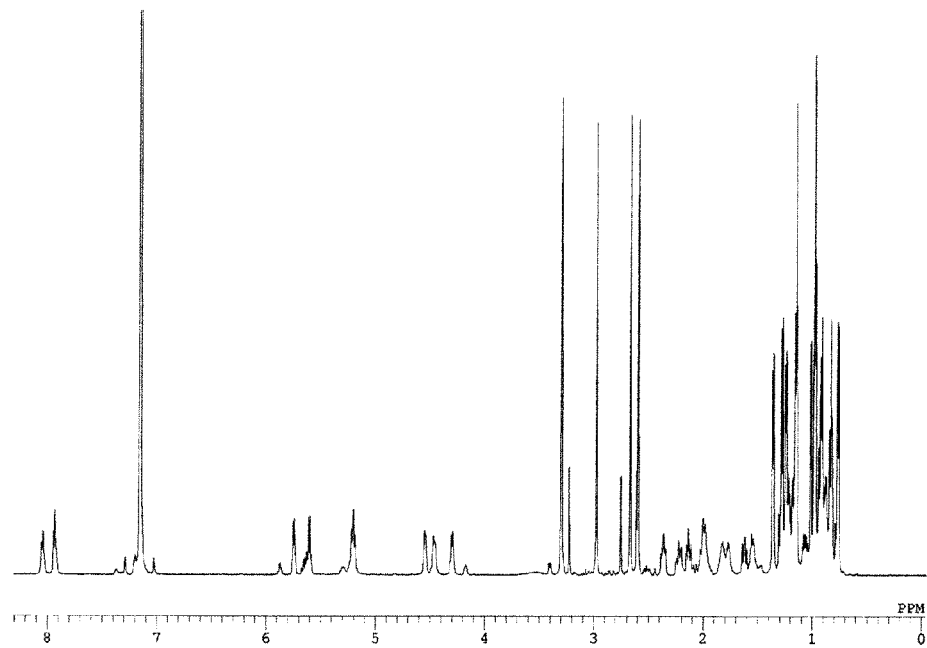
FIG. 3 is a $^1H$ NMR spectrum of cyclic heptapeptide (1b) ($C_6D_6$, 600 MHz).

Under a nitrogen atmosphere, the cyclization precursors thus obtained, 41 mg (0.11 mmol) of HATU, and 15 mg (0.11 mmol) of HOAt were dissolved in 36 mL of dichloromethane and 0.5 mL of DMF, and the mixture was cooled to 0° C. After addition of 43 μL (0.24 mmol) of diisopropylethylamine, the mixture was brought back to room temperature, followed by stirring for 46 hours. The reaction was stopped by addition of 0.12 M hydrochloric acid. The reaction mixture thus obtained was extracted with ethyl acetate (100 mL), and then combined organic layers were washed with saturated sodium bicarbonate solution (15 mL) and saturated saline (15 mL×2), and then dried over anhydrous sodium sulfate. The resulting solution was concentrated under reduced pressure, and the oily substance obtained thereby was purified by column chromatography (silica gel, chloroform-methanol 1/0→39/1→) to yield 43 mg of partially purified products. The partially purified products thus obtained were purified by reverse-phase high performance liquid chromatography [Develosil ODS HG-5 (diameter of 20×250 mm), 50% acetonitrile at a flow rate of 5 mL/min, UV at 215 nm] to yield 24 mg (60%, three steps) of cyclic heptapeptides (1b). FIG. 3 shows $^1$H NMR spectrum of 1b obtained as above.

(1b):major conformer, $^1$H NMR (600 MHz, $C_6D_6$)$^{TM}$8.04 (br d, 1 H), 7.94 (d, J=8.4 Hz, 1 H), 7.20 (br s, 1 H), 5.75 (q, J=6.6 Hz, 1 H), 5.61 (q, J=7.3 Hz, 0 H), 5.20 (m, 2 H), 4.55 (m, 1 H), 4.47 (m, 1 H), 4.30 (q, J=7.3 Hz, 1 H), 3.30 (s, 3 H), 2.98

(s, 3 H), 2.67 (s, 3 H), 2.60 (s, 3 H), 2.36 (m, 1 H), 2.23 (m, 1 H), 2.13 (m, 1 H), 2.00 (m, 2 H), 1.82 (m, 1 H), 1.77 (m, 1 H), 1.62 (m, 1 H), 1.56 (m, 1 H), 1.36 (d, J=6.2 Hz, 3 H), 1.32-0.75 (m, 3 H), 1.28 (d, J=7.0 Hz, 3 H), 1.24 (d, J=6.6 Hz, 3 H), 1.16 (d, J=6.5 Hz, 3 H), 1.15 (d, J=6.6 Hz, 3 H), 0.99 (d, J=7.0 Hz, 3 H), 0.98 (d, J=6.5 Hz, 3 H), 0.92 (d, J=6.6 Hz, 3 H), 0.83 (t, J=7.0 Hz, 3 H), 0.77 (d, J=7.0 Hz, 3 H);

$^{13}$C NMR (150 MHz, $C_6D_6$)δ174.6, 174.2, 174.1, 171.4, 170.8, 169.9, 169.2, 59.1, 54.1, 52.3, 51.6, 51.5, 49.8, 49.7, 43.0, 40.4, 38.7, 35.4, 30.8, 30.0, 29.8, 29.7, 26.4, 25.8, 25.6, 25.4, 23.9, 23.5, 23.3, 23.2, 21.9, 21.3, 15.8, 14.8, 14.1, 13.1, 12.0.

(8) Synthesis of B4c

Following a series of reactions shown below, tripeptide intermediate methyl esters B4c were synthesized. Tripeptide intermediates (B1c) were obtained by alkaline hydrolysis of B4c before use.

[Chemical formula 19]

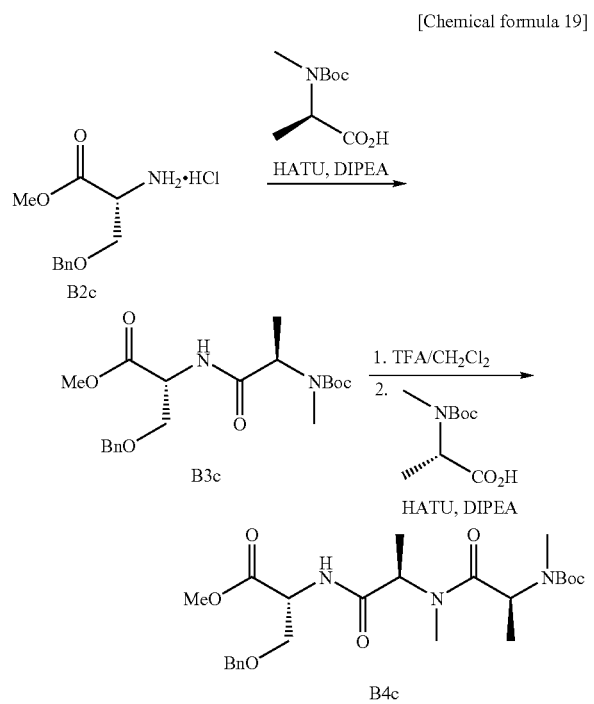

Under a nitrogen atmosphere, 231 mg (1.1 mmol) of D-Ser(OBn)-OMe·HCl (B2c), 224 mg (1.1 mmol) of Boc-NMe-D-Ala-OH, and 564 mg (1.2 mmol) of PyBroP were dissolved in 2.1 mL of dichloromethane, and the mixture was cooled to 0° C. After addition of 570 μL (3.3 mmol) of diisopropylethylamine, the mixture was brought back to room temperature, followed by stirring for one and half hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 4/1→2/1→1/1) to yield 296 mg (68%) of colorless solid dipeptides B3c.

The dipeptides B3c thus obtained (122 mg, 0.31 mmol) were dissolved in 1 mL of dichloromethane under a nitrogen atmosphere, and the mixture was cooled to 0° C. TFA (1 mL) was added to this reaction solution, followed by stirring for one and half hours. The reaction mixture thus obtained was concentrated under reduced pressure and then subjected to azeotropic distillation with toluene three times to give a colorless oily substance. The oily substance thus obtained, 63 mg (0.31 mmol) of Boc-NMe-L-Ala-OH, and 129 mg (0.34 mmol) of HATU were dissolved in 0.5 mL of dichloromethane and 0.1 mL of DMF, and the resulting mixture was cooled to 0° C. After addition of 161 μL (0.93 mmol) of diisopropylethylamine, the mixture was brought back to room temperature, followed by stirring for three hours. The reaction was stopped by addition of 0.12 M hydrochloric acid. The reaction mixture thus obtained was extracted with ethyl acetate (3 mL×3), and then combined organic layers were washed with saturated sodium bicarbonate solution (3 mL) and saturated saline (3 mL×2), and then dried over anhydrous sodium sulfate. The resulting solution was concentrated under reduced pressure, and the oily substance obtained thereby was purified by column chromatography (silica gel, hexane-ether 1/1→1/2→0/1) to yield 94 mg (63%) of colorless oily tripeptides B4c.

(9) Synthesis of Cyclic Heptapeptides (1c)

Following a series of reactions shown below, cyclic heptapeptides (1c) were synthesized.

[Chemical formula 20]

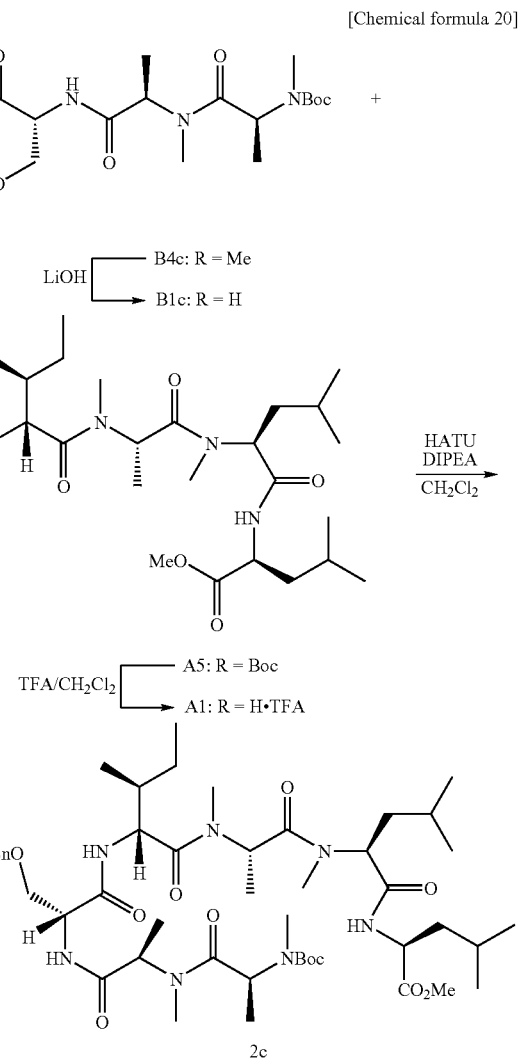

-continued

[Chemical formula 21]

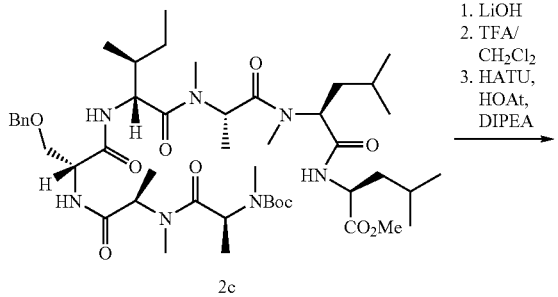

1. LiOH
2. TFA/CH$_2$Cl$_2$
3. HATU, HOAt, DIPEA

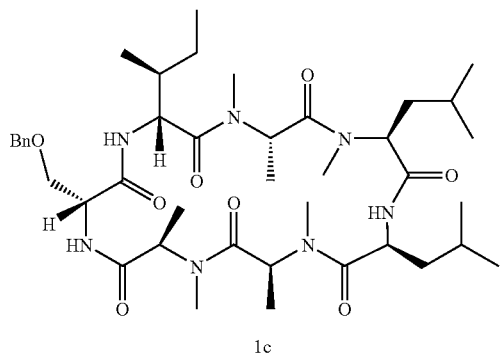

1c

The tripeptides B4c obtained in the above (8) (60 mg, 0.13 mmol) were dissolved in 0.5 mL of THF, 0.5 mL of water, and 2.0 mL of t-BuOH. To this mixture, 26 mg (0.63 mmol) of lithium hydroxide monohydrate was added, followed by stirring for one hour. The reaction mixture thus obtained was made acidic (<pH 3) with addition of 0.12 M hydrochloric acid, followed by extraction with ethyl acetate (5 mL×3), and then combined organic layers were dried over anhydrous sodium sulfate. The resulting solution was concentrated under reduced pressure to yield tripeptide intermediates B1c.

Under a nitrogen atmosphere, the Boc-tetrapeptides A5 (66 mg, 0.12 mmol) was dissolved in 0.5 mL of dichloromethane, and the mixture was cooled to 0° C. TFA (0.5 mL) was added to this reaction solution, followed by stirring for two hours. The reaction mixture thus obtained was concentrated under reduced pressure and then subjected to azeotropic distillation with toluene three times to give colorless oily tetrapeptide intermediates A1. Under a nitrogen atmosphere, A1, B1c, 48 mg (0.13 mmol) of HATU were dissolved in 0.5 mL of dichloromethane and 0.1 mL of DMF, and the mixture was cooled to 0° C. After addition of 60 μL (0.35 mmol) of diisopropylethylamine, the mixture was brought back to room temperature, followed by stirring for 3 hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 1/1→4/6→3/7→0/1→ether-ethyl acetate 1/1→) to yield 92 mg (87%) of colorless pasty heptapeptides 2c.

The heptapeptides 2c thus obtained (46 mg, 50 μmol) were dissolved in 0.25 mL of THF, 0.25 mL of water, and 1.0 mL of t-BuOH. To this mixture, 10 mg (0.25 mmol) of lithium hydroxide monohydrate was added, followed by stirring for two hours. The reaction mixture thus obtained was made acidic (<pH 3) with addition of 0.12 M hydrochloric acid, followed by extraction with ethyl acetate (5 mL×3), and then combined organic layers were dried over anhydrous sodium sulfate. The resulting solution was concentrated under reduced pressure to yield carboxylic acid. Under a nitrogen atmosphere, the carboxylic acid thus obtained was dissolved in 0.5 mL of dichloromethane, and the mixture was cooled to 0° C. TFA (0.5 mL) was added to this reaction solution, followed by stirring for two hours. The reaction mixture thus obtained was concentrated under reduced pressure and then subjected to azeotropic distillation with toluene three times to give colorless oily cyclization precursors.

Figure 4:
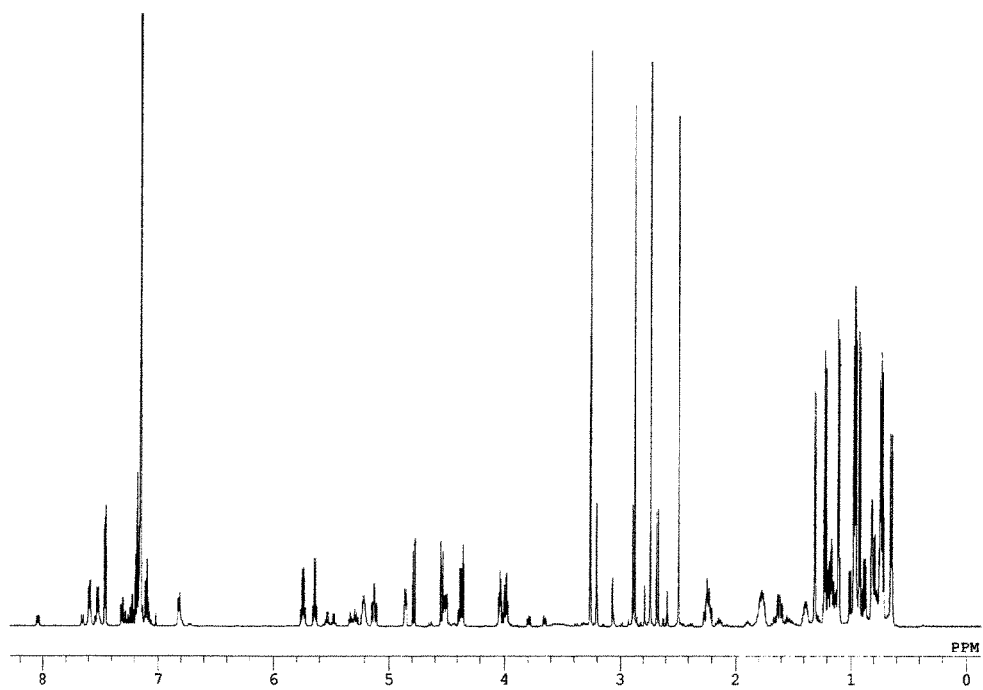
FIG. 4 is a $^1H$ NMR spectrum of cyclic heptapeptide (1c) ($C_6D_6$, 600 MHz).

Under a nitrogen atmosphere, the cyclization precursors thus obtained, 38 mg (0.10 mmol) of HATU, and 14 mg (0.10 mmol) of HOAt were dissolved in 34 mL of dichloromethane and 0.5 mL of DMF, and the mixture was cooled to 0° C. After addition of 40 μL (0.23 mmol) of diisopropylethylamine, the mixture was brought back to room temperature, followed by stirring for 45 hours. The reaction was stopped by addition of 0.12 M hydrochloric acid. The reaction mixture thus obtained was extracted with ethyl acetate (100 mL), and then combined organic layers were washed with saturated sodium bicarbonate solution (15 mL) and saturated saline (15 mL×2), and then dried over anhydrous sodium sulfate. The resulting solution was concentrated under reduced pressure, and the oily substance obtained thereby was purified by column chromatography (silica gel, chloroform-methanol 1/0→39/1→) to yield 43 mg of partially purified products. The partially purified products thus obtained were purified by reverse-phase high performance liquid chromatography [Develosil ODS HG-5 (diameter of 20×250 mm), 55% acetonitrile at a flow rate of 5 mL/min, UV at 215 nm] to yield 22 mg (56%, three steps) of cyclic heptapeptides (1c). FIG. 4 shows $^1$H NMR spectrum of 1c obtained as above.

(1c):major conformer, $^1$H NMR (600 MHz, C$_6$D$_6$)δ7.60 (d, J=7.7 Hz, 1 H), 7.53 (d, J=8.8 Hz, 1 H), 7.46 (d, J=7.3 Hz, 2 H), 7.19 (t, J=7.3 Hz, 2 H), 7.10 (t, J=7.3 Hz, 1 H), 6.82 (d, J=8.5 Hz, 1 H), 5.75 (q, J=6.6 Hz, 1 H), 5.65 (q, J=7.3 Hz, 1 H), 5.22 (m, 1 H), 5.13 (m, 1 H), 4.86 (dd, J=2.9, 8.4 Hz, 1 H), 4.79 (d, J=11.0 Hz, 1 H), 4.55 (d, J=11.0 Hz, 1 H), 4.52 (dd, J=5.2, 10.3 Hz, 1 H), 4.38 (q, J=7.7 Hz, 1 H), 4.04 (m, 1 H), 3.99 (m, 1 H), 3.26 (s, 3 H), 2.88 (s, 3 H), 2.74 (s, 3 H), 2.50 (s, 3 H), 2.25 (m, 1 H), 1.78 (m, 2 H), 1.64 (m, 1 H), 1.39 (m, 1 H), 1.31 (d, J=6.6 Hz, 3 H), 1.25-0.75 (m, 3 H), 1.23 (d, J=7.0 Hz, 3 H), 1.11 (d, J=6.6 Hz, 3 H), 0.97 (d, J=6.6 Hz, 3 H), 0.93 (d, J=6.6 Hz, 3 H), 0.75 (d, J=7.3 Hz, 3 H), 0.73 (t, J=7.7 Hz, 3 H), 0.65 (d, J=6.5 Hz, 3 H);

$^{13}$C NMR (150 MHz, C$_6$D$_6$)δ174.7, 174.1, 171.6, 171.5, 170.2, 169.8, 169.4, 138.1, 128.6, 128.59 (2C), 128.57 (2C), 73.8, 71.2, 58.4, 52.4, 52.2, 51.8, 51.1, 49.9, 49.6, 40.0, 38.0, 35.1, 30.1, 29.7, 29.6, 29.5, 26.9, 25.9, 25.1, 23.8, 23.4, 22.5, 21.3, 16.1, 14.1, 13.7, 13.3, 11.7.

(10) Synthesis of B4d

Following a series of reactions shown below, tripeptide intermediate methyl esters B4d were synthesized. Tripeptide intermediates (B1d) were obtained by alkaline hydrolysis of B4d before use.

[Chemical formula 22]

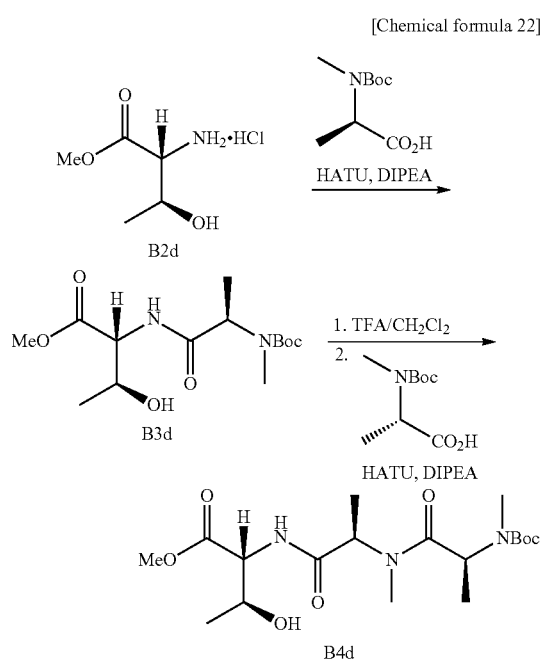

Under a nitrogen atmosphere, 300 mg (1.3 mmol) of Boc-D-Thr-OMe.HCl (B2d) was dissolved in 1 mL of dichloromethane, and the mixture was cooled to 0° C. TFA (1 mL) was added to this reaction solution, followed by stirring for two hours. The reaction mixture thus obtained was concentrated under reduced pressure and then subjected to azeotropic distillation with toluene three times to give a colorless oily substance. The oily substance thus obtained, 260 mg (1.3 mmol) of Boc-NMe-L-Ala-OH, and 532 mg (1.4 mmol) of HATU were dissolved in 1.5 mL of dichloromethane, and the resulting mixture was cooled to 0° C. After addition of 668 μL (3.8 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 1/1→1/2→0/1) to yield 231 mg (57%) of colorless solid dipeptides B3d.

The dipeptides thus obtained (214 mg, 0.67 mmol) were dissolved in 1 mL of dichloromethane under a nitrogen atmosphere, and the mixture was cooled to 0° C. TFA (1 mL) was added to this reaction solution, followed by stirring for two hours. The reaction mixture thus obtained was concentrated under reduced pressure and then subjected to azeotropic distillation with toluene three times to give a colorless oily substance. The oily substance thus obtained, 137 mg (0.67 mmol) of Boc-NMe-L-Ala-OH, and 280 mg (0.73 mmol) of HATU were dissolved in 1.5 mL of dichloromethane and 0.2 mL of DMF, and the resulting mixture was cooled to 0° C. After addition of 348 μL (2.0 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 1/1→1/2→0/1) to yield 138 mg (51%) of colorless oily tripeptides B4d.

(11) Synthesis of Cyclic Heptapeptides (1d)

Following a series of reactions shown below, cyclic heptapeptides (1d) were synthesized.

[Chemical formula 23]

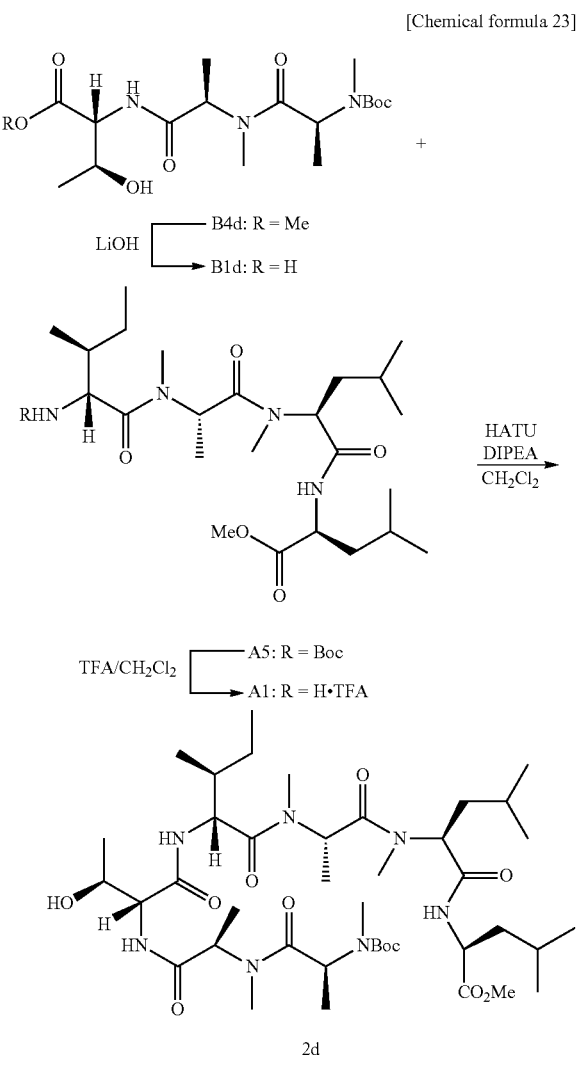

[Chemical formula 24]

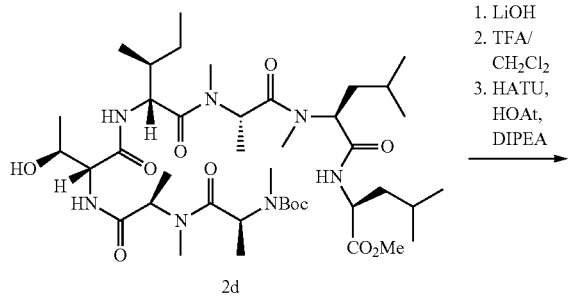

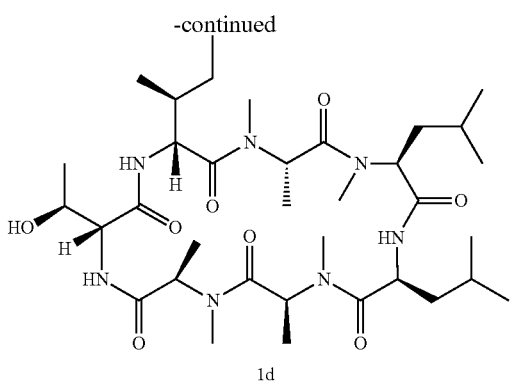

1d

The tripeptides B4d obtained in the above (10) (55 mg, 0.14 mmol) were dissolved in 0.5 mL of THF, 0.5 mL of water, and 2.0 mL of t-BuOH. To this mixture, 28 mg (0.68 mmol) of lithium hydroxide monohydrate was added, followed by stirring for one and half hours. The reaction mixture thus obtained was made acidic (<pH 3) with addition of 0.12 M hydrochloric acid, followed by extraction with ethyl acetate (5 mL×3), and then combined organic layers were dried over anhydrous sodium sulfate. The resulting solution was concentrated under reduced pressure to yield tripeptide intermediates Bid.

Under a nitrogen atmosphere, the Boc-tetrapeptides A5 (78 mg, 0.14 mmol) was dissolved in 0.5 mL of dichloromethane, and the mixture was cooled to 0° C. TFA (0.5 mL) was added to this reaction solution, followed by stirring for two hours. The reaction mixture thus obtained was concentrated under reduced pressure and then subjected to azeotropic distillation with toluene three times to give colorless oily tetrapeptide intermediates A1.

Under a nitrogen atmosphere, A1, B1d, and 57 mg (0.15 mmol) of HATU were dissolved in 0.5 mL of dichloromethane and 0.1 mL of DMF, and the mixture was cooled to 0° C. After addition of 71 µL (0.41 mmol) of diisopropylethylamine, the mixture was brought back to room temperature, followed by stirring for two hours. The reaction was stopped by addition of 0.12 M hydrochloric acid. The reaction mixture thus obtained was extracted with ethyl acetate (5 mL×3), and then combined organic layers were washed with saturated sodium bicarbonate solution (5 mL) and saturated saline (5 mL×2), and then dried over anhydrous sodium sulfate. The resulting solution was concentrated under reduced pressure, and the oily substance obtained thereby was purified by column chromatography (silica gel, hexane-ether 1/1→0/1→ether-ethyl acetate 9/1→5/1) to yield 74 mg (69%) of colorless pasty heptapeptides 2d.

The heptapeptides 2d thus obtained (53 mg, 63 µmol) were dissolved in 0.25 mL of THF, 0.25 mL of water, and 1.0 mL of t-BuOH. To this mixture, 13 mg (0.31 mmol) of lithium hydroxide monohydrate was added, followed by stirring for two hours. The reaction mixture thus obtained was made acidic (<pH 3) with addition of 0.12 M hydrochloric acid, followed by extraction with ethyl acetate (5 mL×3), and then combined organic layers were dried over anhydrous sodium sulfate. The resulting solution was concentrated under reduced pressure to yield carboxylic acid. Under a nitrogen atmosphere, the carboxylic acid thus obtained was dissolved in 0.5 mL of dichloromethane, and the mixture was cooled to 0° C. TFA (0.5 mL) was added to this reaction solution, followed by stirring for two hours. The reaction mixture thus obtained was concentrated under reduced pressure and then subjected to azeotropic distillation with toluene three times to give colorless oily cyclization precursors.

Figure 5:
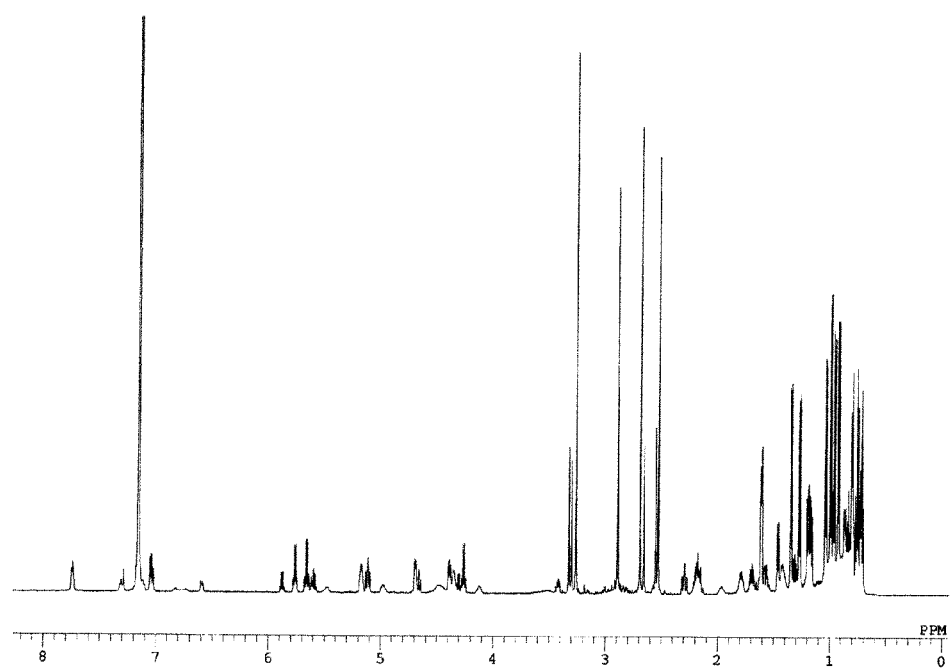
FIG. 5 is a $^1H$ NMR spectrum of cyclic heptapeptide (1d) ($C_6D_6$, 600 MHz).

Under a nitrogen atmosphere, the cyclization precursors thus obtained, 48 mg (0.13 mmol) of HATU, and 17 mg (0.13 mmol) of HOAt were dissolved in 42 mL of dichloromethane and 0.5 mL of DMF, and the mixture was cooled to 0° C. After addition of 49 µL (0.28 mmol) of diisopropylethylamine, the mixture was brought back to room temperature, followed by stirring for 45 hours. The reaction was stopped by addition of 0.12 M hydrochloric acid. The reaction mixture thus obtained was extracted with ethyl acetate (100 mL), and then combined organic layers were washed with saturated sodium bicarbonate solution (15 mL) and saturated saline (15 mL×2), and then dried over anhydrous sodium sulfate. The resulting solution was concentrated under reduced pressure, and the oily substance obtained thereby was purified by column chromatography (silica gel, chloroform-methanol 1/0→39/1→) to yield 51 mg of partially purified products. The partially purified products thus obtained were purified by reverse-phase high performance liquid chromatography [Develosil ODS HG-5 (diameter of 20×250 mm), 60% acetonitrile at a flow rate of 5 mL/min, UV at 215 nm] to yield 25 mg (56%, three steps) of cyclic heptapeptides (1d). FIG. 5 shows $^1$H NMR spectrum of 1d obtained as above.

(1d):major conformer, $^1$H NMR (600 MHz, C$_6$D$_6$)δ7.74 (br, 1 H), 7.05 (d, J=8.8 Hz, 1 H), 5.76 (q, J=6.5 Hz, 1 H), 5.66 (q, J=8.5 Hz, 1 H), 5.17 (m, 1 H), 5.11 (m, 1 H) 4.69 (d d, J=3.7, 7.7 Hz, 1 H), 4.48 (m, 1H), 4.38 (m, 1 H), 4.35 br, 1 H), 4.26 (q, J=7.3 Hz, 1 H), 3.26 (s, 3 H), 2.89 (s, 3 H), 2.69 (s, 3 H), 2.53 (s, 3 H), 2.29 (ddd, J=3.7, 11.7, 15.4 Hz, 1 H), 2.18 (m, 2 H), 1.79 (m, 1 H), 1.69 (m, 1 H), 1.61 (d, J=6.6 Hz, 3 H), 1.42 (m, 1 H), 1.35 (d, J=6.6 Hz, 3 H), 1.35-0.98 (m, 3H), 1.27 (d, J=7.0 Hz, 3 H), 1.04 (d, J=6.6 Hz, 3 H), 1.00 (d, J=6.6 Hz, 3 H), 0.96 (d, J=6.6 Hz, 3 H), 0.93 (d, J=7.0 Hz, 3 H), 0.81 (d, J=6.2 Hz, 3 H), 0.76 (d, J=7.3 Hz, 3 H), 0.72 (t, J=7.3 Hz, 3 H), an amide NH proton could not be specified;

$^{13}$C NMR (150 MHz, C$_6$D$_6$)δ174.6, 174.3, 171.8, 171.4, 169.9, 169.8, 169.5, 69.2, 59.0, 57.8, 53.3, 51.9, 51.2, 50.2, 49.9, 40.3, 37.8, 34.8, 30.6, 30.1, 29.6 (2C), 26.9, 25.9, 25.2, 23.6, 23.4, 23.3, 21.2, 18.5, 15.5, 14.2, 14.1, 13.2, 11.7.

(12) Synthesis of 1e

Following a series of reactions shown below, cyclic heptapeptides (1e) were synthesized.

[Chemical formula 25]

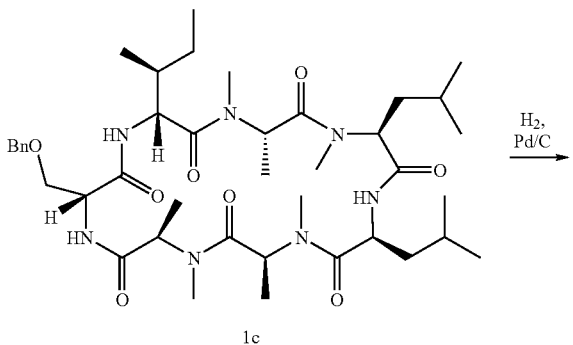

1e

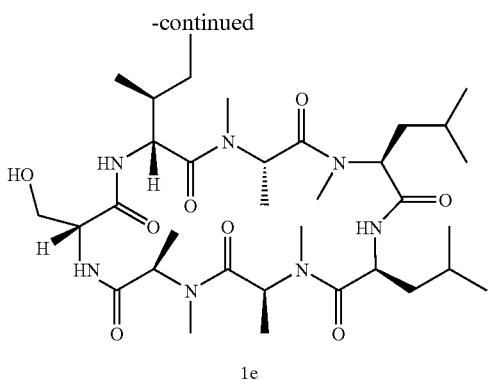

1e

Figure 6:
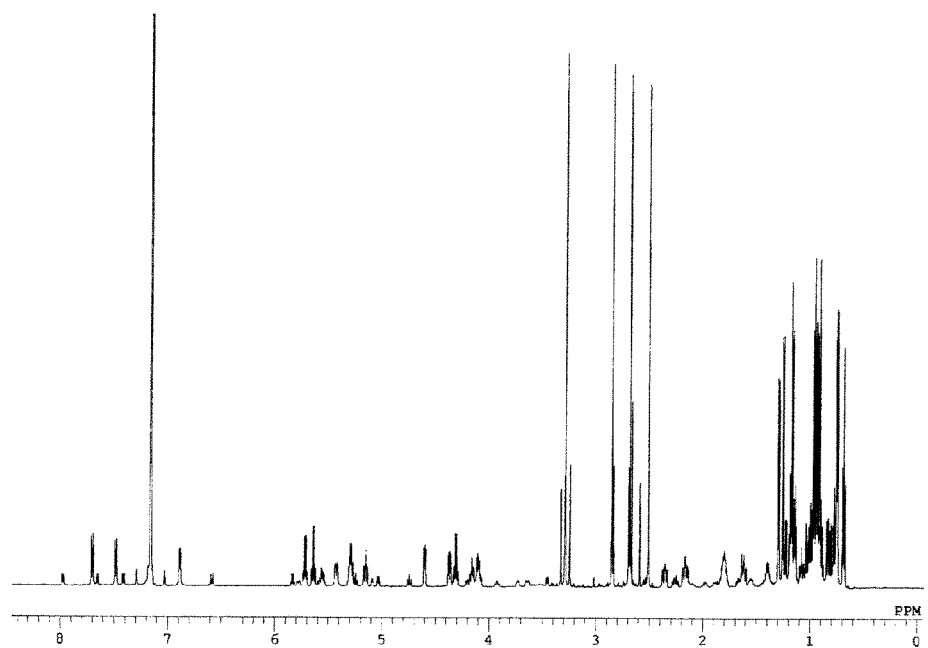
FIG. 6 is a $^1H$ NMR spectrum of cyclic heptapeptide (1e) ($C_6D_6$, 600 MHz).

Under a nitrogen atmosphere, the 1c obtained as above (10 mg, 12.7 mmol) and 10 mg of 5% Pd/C were dissolved in 1 mL of methanol. The atmosphere in the above reaction system was replaced with hydrogen gas, followed by stirring for three and half days. Then, the reaction mixture was filtrated through Celite, and the filtrate thus obtained was concentrated under reduced pressure. The oily substance obtained thereby was purified by reverse-phase high performance liquid chromatography [Develosil ODS HG-5 (diameter of 20×250 mm), 50% acetonitrile at a flow rate of 5 mL/min, UV at 215 nm] to yield 6.5 mg (74%) of cyclic heptapeptides (1e). FIG. 6 shows $^1$H NMR spectrum of 1e obtained as above.

(1e):major conformer, $^1$H NMR (600 MHz, $C_6D_6$)δ7.70 (d, J=9.2 Hz, 1 H), 7.49 (d, J=8.8 Hz, 1 H), 6.89 (d, J=7.0 Hz, 1 H), 5.72 (q, J=6.5 Hz, 1 H), 5.64 (q, J=7.3 Hz, 1 H), 5.43 (m, 1 H), 5.28 (m, 1 H), 5.15 (m, 1 H), 4.60 (dd, J=3.7, 7.0 Hz, 1 H), 4.37 (dd, J=4.4, 11.0 Hz, 1 H), 4.32 (q, J=7.3 Hz, 1 H), 4.16 (m, 1 H), 4.10 (dd, J=7.0, 11.7 Hz, 1 H), 3.29 (s, 3 H), 2.85 (s, 3 H), 2.68 (s, 3 H), 2.51 (s, 3 H), 2.36 (m, 1 H), 2.17 (m, 1 H), 1.80 (m, 2 H), 1.61 (m, 1 H), 1.40 (m, 1 H), 1.29 (d, J=6.2 Hz, 3 H), 1.25 (d, J=7.0 Hz, 3 H), 1.24-0.74 (m, 12 H), 1.17 (d, J=6.6 Hz, 3 H), 0.75 (d, J=7.3 Hz, 3 H), 0.74 (d, J=6.5 Hz, 3 H), 0.69 (t, J=7.3 Hz, 3 H);

$^{13}$C NMR (150 MHz, $C_6D_6$)δ174.7, 174.3, 173.2, 172.5, 169.8, 169.2, 169.0, 64.1, 59.2, 54.7 (2C), 51.9, 51.3, 49.9 (2C), 40.6, 37.7, 34.2, 30.6, 29.7 (2C), 29.5, 26.7, 26.1, 25.3, 23.8, 23.3, 22.5, 21.4, 15.8, 14.0, 13.8, 13.2, 11.7.

3. Evaluation of the Effects of the Novel Cyclic Heptapeptide (A Preadipocyte Differentiation-Inhibitory Effect and an Adipocyte Fat Accumulation-Inhibitory Effect)

Murine preadipocytes (3T3-L1) have such a property as to accumulate fat following differentiation. In the present test, while differentiation of 313-L1 preadipocytes was induced by insulin and the like, test compounds were simultaneously added. Then, an amount of fat in the cells was measured to evaluate that the test compounds exert inhibition of differentiation of the preadipocytes or an inhibitory effect on fat accumulation following differentiation. In this test, in a case where cells die due to the test compounds, there is concern that the test might unintentionally result in a low fat accumulation rate, which is seemingly a favorable result. In order to judge presence or absence of cytotoxicity as described above, evaluation based on a cell survival rate was adopted in the present test, and in this way the present test was elaborated so that a compound with low cytotoxicity that would strongly inhibit fat accumulation could be efficiently assayed. Also, fat accumulation was observed under a microscope from time to time during the test.

Preadipocytes (3T3-L1) were cultured to confluence in the presence of 5% $CO_2$ at 37° C. for two days in 150 μL of culture media (DMEM containing 10% fetal bovine serum (glucose concentration of 4500 mg/mL)) in two 96-well microplates. Then, with respect to both plates, the culture media were aspirated and replaced with 150 μL of differentiation-inducing media containing a certain concentration of test compounds (DMEM containing 10% fetal bovine serum (glucose concentration of 4500 mg/mL) in which 1 μM dexamethasone, 10 μg/mL insulin, and 0.5 mM 3-isobutyl-1-methylxanthine were dissolved). Normally, methanol solution containing a 200-fold concentration of test compounds (1a, 1b, 1c, 1d, and 1e) was prepared, and 7.5 μL of the solution was added with respect to 1.5 mL of the differentiation-inducing media. At this time, a well that was not replaced with the differentiation-inducing medium and a well to which only methanol was added instead of a sample solution were prepared as a control. The plates were cultured in the presence of 5% $CO_2$ at 37° C. for seven days. Thereafter, one plate was served for measurement of an amount of fat, and the other plate was served for measurement of a survival rate.

To each well of the plate for measurement of an amount of fat, 10 μL of 2% Triton X-100 was added, and the plate was left to stand for 30 minutes. Subsequently, the plate was sealed with a sealing tape (a product of Asahi Techno Glass Corporation) and sonicated for one minute in an ultrasonic cleaner. Subsequently, 20 μL of solution was collected from each well and added to a 96-well microplate in which 150 μL of Triglyceride E-test Wako (a product of Wako Pure Chemical Industries, Ltd.), a coloring reagent, had been added to each well, and then the plate was incubated at 37° C. for 30 minutes, after which absorbance (at 630 nm, control at 690 nm) was measured by a plate reader. A ratio of absorbance in a compound-added group to absorbance in a compound-free group was obtained as a percentage, which was provided as a fat accumulation rate. Fat accumulation rates with respect to a concentration in each sample were represented as a semilogarithmic graph. From this graph a compound concentration at which a fat accumulation rate was 50% was read off, which was provided as a 50% effective concentration (EC50). EC50 values obtained for each compound was shown in FIG. 7. It can be interpreted that the smaller the EC50 value is, the stronger the inhibitory effect on differentiation of adipocytes or on fat accumulation in adipocytes is.

To each well of the plate for measurement of a survival rate, 5 μL of Cell counting kit-8 (a product of Dojindo Laboratories) was added, and then the plate was incubated at 37° C. for four hours, after which absorbance (at 450 nm) was measured by a plate reader. A ratio of absorbance in a compound-added group to absorbance in a compound-free group was obtained as a percentage, which was provided as a cell survival rate. Cell survival rates with respect to a concentration of each compound were represented as a semilogarithmic graph. From this graph, a compound concentration at which a cell survival rate was 50% was read off, which was provided as a 50% inhibitory concentration (IC50). IC50 values obtained for each compound was shown in FIG. 7. It can be interpreted that the larger the IC50 value is, the less toxic the compound is against adipocytes.

Furthermore, in order to evaluate usefulness of the compounds, IC50/EC50 values were obtained and shown in FIG. 7. The less toxic the compound is against cells, the larger the value is, and further, the stronger the inhibitory effect on differentiation or the inhibitory effect on fat accumulation, the larger the value is. That is, it can be interpreted that the larger the IC50/EC50 value is, the safer the compound is as a medicine, and therefore the more potent the compound is.

From the EC50 values, it is understood that any of the novel compounds (1a, 1b, 1c, 1d, and 1e) excellently exerts an inhibitory effect on differentiation of adipocytes or on fat accumulation in adipocytes (FIG. 7). Further, the IC50 values of the novel compounds are higher than that of ternatin, based on which it is understood that the compounds have a low cytotoxicity (FIG. 7). Focusing on the IC50/EC50 values, which serve as an indication of safety as a medicine, it can be said that the novel compounds are as potent as or more potent than ternatin (FIG. 7).

INDUSTRIAL APPLICABILITY

Since the cyclic heptapeptide of the present invention inhibits the differentiation of preadipocytes and the accumulation of fat in adipocytes, it is useful for the prophylaxis or treatment (inhibition and improvement) of obesity. Also, the cyclic heptapeptide of the present invention is useful as a lead compound for the development of a prophylactic or therapeutic medicine for obesity. Furthermore, the cyclic heptapeptide of the present invention is useful as a reagent to be used in studies for elucidating the molecular mechanisms and fat-accumulation mechanisms in adipocytes, and the like. In addition, since the cyclic heptapeptide of the present invention can be used as a reagent that acts at a point of action at which a useful effect is elicited, it is useful as a tool for elucidating operational mechanisms.

The present invention is not limited by the above-described embodiments of the invention or by the description of the Examples in any way. Various modified embodiments are encompassed in the present invention to the extent that a person skilled in the art would be able to easily conceive without going beyond the description of the Claims.

The contents of papers, the publication of patent applications, and the patent gazette stated in the present specification are wholly incorporated herein by reference.

The invention claimed is:

1. A cyclic heptapeptide represented by the following formula;

[Chemical formula 1]

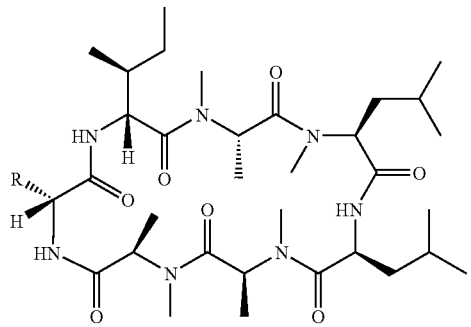

wherein R is $CH_3$, $CH_2CH(CH_3)_2$, $CH_2OCH_2C_6H_5$, or $CH_2OH$.

2. A composition that contains the cyclic heptapeptide according to claim 1 as an active ingredient.

3. The composition according to claim 2, wherein the composition is food product comprising the cyclic heptapeptide and a grain, vegetable, meat, processed food, snack, milk, soft drink, alcoholic beverage, nutritional supplement, food supplement, or energy drink.

4. The composition of claim 3, wherein the cyclic heptapeptide is provided in the form of a powder, granule, tablet, paste, or liquid.

5. The composition of claim 2, wherein the composition is a pharmaceutical composition comprising the cyclic heptapeptide and one or more of the group consisting of pharmaceutically-acceptable carrier, excipient, disintegrant, buffer, emulsifier, suspension agent, pain-killing agent, stabilizer, preservative, antiseptic agent, and physiological saline.

6. The composition of claim 5, wherein the composition is a tablet, a powder, a fine-granule, a granule, a capsule, a syrup, an injection, an external agent, or a suppository.

7. The composition of claim 5, wherein the composition is formulated for oral or parenteral administration.

8. The composition of claim 2, wherein the composition is a cosmetic composition comprising the cyclic heptapeptide and one or more ingredients that are normally used in a cosmetic agent selected from the group consisting of fat, oil, mineral oil, vaseline, squalane, lanolin, beeswax, denatured alcohol, dextrin palmitate, glycerin, a glycerin fatty acid ester, ethylene glycol, paraben, camphor, menthol, vitamins, zinc oxide, titanium oxide, benzoic acid, edetic acid, chamomile oil, carrageenan, chitin powder, chitosan, perfume, and colorant.

9. The composition of claim 8, wherein the composition is an emulsion for the face or body, a toner, a cream, a lotion, an essence, an oil, a pack, a sheet, or a cleansing agent.

10. A method for inhibiting fat accumulation in an adipocyte, the method comprising administering to an adipocyte an effective amount of a composition of claim 2.

11. The method of claim 10, wherein the adipocyte is in vitro.

12. The method of claim 10, wherein the preadipocyte is in a subject.

13. The method of claim 12, wherein the subject is a human.

14. The method of claim 12, wherein the composition is a food product, a pharmaceutical composition, or a cosmetic composition.

15. The method of claim 12, wherein inhibiting fat accumulation in an adipocyte treats obesity.

16. A method for inhibiting preadipocyte differentiation, the method comprising administering to a preadipocyte an effective amount of a composition of claim 2.

17. The method of claim 16, wherein the preadipocyte is in vitro.

18. The method of claim 16, wherein the preadipocyte is in a subject.

19. The method of claim 18, wherein the subject is a human.

20. The method of claim 18, wherein inhibiting preadipocyte differentiation treats obesity.

* * * * *

```
                        SEQUENCE LISTING

<160> NUMBER OF SEQ ID NOS: 6

<210> SEQ ID NO 1
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-allo-Ile
<220> FEATURE:
<221> NAME/KEY: MOD_RES
<222> LOCATION: (2)..(2)
<223> OTHER INFORMATION: NMe-L-Ala
<220> FEATURE:
<221> NAME/KEY: MOD_RES
<222> LOCATION: (3)..(3)
<223> OTHER INFORMATION: NMe-L-Leu
<220> FEATURE:
<221> NAME/KEY: MOD_RES
<222> LOCATION: (5)..(5)
<223> OTHER INFORMATION: NMe-L-Ala
<220> FEATURE:
<221> NAME/KEY: MOD_RES
<222> LOCATION: (6)..(6)
<223> OTHER INFORMATION: NMe-D-Ala
<220> FEATURE:
<221> NAME/KEY: MOD_RES
<222> LOCATION: (7)..(7)
<223> OTHER INFORMATION: Xaa is D-Ala, D-Leu, D-Ser(OBn), D-Thr or
      D-Ser.

<400> SEQUENCE: 1

Xaa Xaa Xaa Leu Xaa Xaa Xaa
1               5

<210> SEQ ID NO 2
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-allo-Ile
<220> FEATURE:
<221> NAME/KEY: MOD_RES
<222> LOCATION: (2)..(2)
<223> OTHER INFORMATION: NMe-L-Ala
```

```
<220> FEATURE:
<221> NAME/KEY: MOD_RES
<222> LOCATION: (3)..(3)
<223> OTHER INFORMATION: NMe-L-Leu
<220> FEATURE:
<221> NAME/KEY: MOD_RES
<222> LOCATION: (5)..(5)
<223> OTHER INFORMATION: NMe-L-Ala
<220> FEATURE:
<221> NAME/KEY: MOD_RES
<222> LOCATION: (6)..(6)
<223> OTHER INFORMATION: NMe-D-Ala
<220> FEATURE:
<221> NAME/KEY: MOD_RES
<222> LOCATION: (7)..(7)
<223> OTHER INFORMATION: D-Ala

<400> SEQUENCE: 2

Xaa Xaa Xaa Leu Xaa Xaa Xaa
1               5

<210> SEQ ID NO 3
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-allo-Ile
<220> FEATURE:
<221> NAME/KEY: MOD_RES
<222> LOCATION: (2)..(2)
<223> OTHER INFORMATION: NMe-L-Ala
<220> FEATURE:
<221> NAME/KEY: MOD_RES
<222> LOCATION: (3)..(3)
<223> OTHER INFORMATION: NMe-L-Leu
<220> FEATURE:
<221> NAME/KEY: MOD_RES
<222> LOCATION: (5)..(5)
<223> OTHER INFORMATION: NMe-L-Ala
<220> FEATURE:
<221> NAME/KEY: MOD_RES
<222> LOCATION: (6)..(6)
<223> OTHER INFORMATION: NMe-D-Ala
<220> FEATURE:
<221> NAME/KEY: MOD_RES
<222> LOCATION: (7)..(7)
<223> OTHER INFORMATION: D-Leu

<400> SEQUENCE: 3

Xaa Xaa Xaa Leu Xaa Xaa Xaa
1               5

<210> SEQ ID NO 4
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-allo-Ile
<220> FEATURE:
<221> NAME/KEY: MOD_RES
<222> LOCATION: (2)..(2)
<223> OTHER INFORMATION: NMe-L-Ala
<220> FEATURE:
<221> NAME/KEY: MOD_RES
<222> LOCATION: (3)..(3)
<223> OTHER INFORMATION: NMe-L-Leu
<220> FEATURE:
<221> NAME/KEY: MOD_RES
```

-continued

```
<222> LOCATION: (5)..(5)
<223> OTHER INFORMATION: NMe-L-Ala
<220> FEATURE:
<221> NAME/KEY: MOD_RES
<222> LOCATION: (6)..(6)
<223> OTHER INFORMATION: NMe-D-Ala
<220> FEATURE:
<221> NAME/KEY: MOD_RES
<222> LOCATION: (7)..(7)
<223> OTHER INFORMATION: D-Ser(OBn)

<400> SEQUENCE: 4

Xaa Xaa Xaa Leu Xaa Xaa Xaa
1               5

<210> SEQ ID NO 5
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-allo-Ile
<220> FEATURE:
<221> NAME/KEY: MOD_RES
<222> LOCATION: (2)..(2)
<223> OTHER INFORMATION: NMe-L-Ala
<220> FEATURE:
<221> NAME/KEY: MOD_RES
<222> LOCATION: (3)..(3)
<223> OTHER INFORMATION: NMe-L-Leu
<220> FEATURE:
<221> NAME/KEY: MOD_RES
<222> LOCATION: (5)..(5)
<223> OTHER INFORMATION: NMe-L-Ala
<220> FEATURE:
<221> NAME/KEY: MOD_RES
<222> LOCATION: (6)..(6)
<223> OTHER INFORMATION: NMe-D-Ala
<220> FEATURE:
<221> NAME/KEY: MOD_RES
<222> LOCATION: (7)..(7)
<223> OTHER INFORMATION: D-Thr

<400> SEQUENCE: 5

Xaa Xaa Xaa Leu Xaa Xaa Xaa
1               5

<210> SEQ ID NO 6
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-allo-Ile
<220> FEATURE:
<221> NAME/KEY: MOD_RES
<222> LOCATION: (2)..(2)
<223> OTHER INFORMATION: NMe-L-Ala
<220> FEATURE:
<221> NAME/KEY: MOD_RES
<222> LOCATION: (3)..(3)
<223> OTHER INFORMATION: NMe-L-Ala
<220> FEATURE:
<221> NAME/KEY: MOD_RES
<222> LOCATION: (5)..(5)
<223> OTHER INFORMATION: NMe-L-Ala
<220> FEATURE:
<221> NAME/KEY: MOD_RES
<222> LOCATION: (6)..(6)
<223> OTHER INFORMATION: NMe-D-Ala
```

```
<220> FEATURE:
<221> NAME/KEY: MOD_RES
<222> LOCATION: (7)..(7)
<223> OTHER INFORMATION: D-Ser

<400> SEQUENCE: 6

Xaa Xaa Xaa Leu Xaa Xaa Xaa
1               5
```